(12) United States Patent
Coric et al.

(10) Patent No.: US 11,965,031 B2
(45) Date of Patent: *Apr. 23, 2024

(54) USE OF ANTI-PD-1 ANTIBODY IN COMBINATION WITH ANTI-CD27 ANTIBODY IN CANCER TREATMENT

(71) Applicants: Bristol-Myers Squibb Company, Princeton, NJ (US); Celldex Therapeutics, Inc., Hampton, NJ (US)

(72) Inventors: Vladimir Coric, Madison, CT (US); Tibor Keler, Pipersville, PA (US); Thomas Davis, Centreville, MD (US)

(73) Assignees: Bristol-Myers Squibb Company, Princeton, NJ (US); Celldex Therapeutics, Inc., Hampton, NJ (US)

( * ) Notice: Subject to any disclaimer, the term of this patent is extended or adjusted under 35 U.S.C. 154(b) by 616 days.

This patent is subject to a terminal disclaimer.

(21) Appl. No.: 17/099,547

(22) Filed: Nov. 16, 2020

(65) Prior Publication Data

US 2021/0139597 A1 May 13, 2021

Related U.S. Application Data

(63) Continuation of application No. 16/505,288, filed on Jul. 8, 2019, now abandoned, which is a continuation of application No. 15/384,205, filed on Dec. 19, 2016, now Pat. No. 10,392,442.

(60) Provisional application No. 62/268,990, filed on Dec. 17, 2015.

(51) Int. Cl.
| | |
|---|---|
| C07K 16/28 | (2006.01) |
| A61K 39/00 | (2006.01) |
| A61K 39/395 | (2006.01) |
| A61K 45/06 | (2006.01) |
| A61P 35/00 | (2006.01) |
| C07K 16/30 | (2006.01) |

(52) U.S. Cl.
CPC .......... *C07K 16/2878* (2013.01); *A61K 39/00* (2013.01); *A61K 39/0008* (2013.01); *A61K 39/0011* (2013.01); *A61K 39/001129* (2018.08); *A61K 39/00115* (2018.08); *A61K 39/39558* (2013.01); *A61K 45/06* (2013.01); *A61P 35/00* (2018.01); *C07K 16/2818* (2013.01); *C07K 16/3023* (2013.01); *C07K 16/3046* (2013.01); *C07K 16/3053* (2013.01); *C07K 16/3069* (2013.01); *A61K 2039/505* (2013.01); *A61K 2039/507* (2013.01); *A61K 2039/545* (2013.01); *C07K 2317/21* (2013.01); *C07K 2317/73* (2013.01); *C07K 2317/75* (2013.01); *C07K 2317/76* (2013.01)

(58) Field of Classification Search
CPC ........ C07K 16/2878; A61K 39/001129; A61K 39/00115; A61K 39/39558
See application file for complete search history.

(56) References Cited

U.S. PATENT DOCUMENTS

| | | |
|---|---|---|
| 6,808,710 B1 | 10/2004 | Wood et al. |
| 7,488,802 B2 | 2/2009 | Collins et al. |
| 7,595,048 B2 | 9/2009 | Honjo et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,757 B2 | 5/2012 | Finnefrock et al. |
| 8,354,509 B2 | 1/2013 | Carven et al. |
| 8,383,796 B2 | 2/2013 | Korman et al. |
| 8,609,089 B2 | 12/2013 | Langermann et al. |
| 8,728,474 B2 | 5/2014 | Honjo et al. |
| 8,779,105 B2 | 7/2014 | Korman et al. |
| 8,900,587 B2 | 12/2014 | Carven et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,169,325 B2 | 10/2015 | Keler et al. |
| 9,212,224 B2 | 12/2015 | Cogswell et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,393,301 B2 | 7/2016 | Honjo et al. |

(Continued)

FOREIGN PATENT DOCUMENTS

| | | |
|---|---|---|
| WO | WO-2004004771 A1 | 1/2004 |
| WO | WO-2006121168 A1 | 11/2006 |

(Continued)

OTHER PUBLICATIONS

He et al., Development of PD-1/PD-L1 Pathway in Tumor Immune Microenvironment and Treatment for Non-Small Cell Lung Cancer, Scientific Reports, 5:13110, Publication Date: Aug. 17, 2015 (Year: 2015).*

Brahmer, J.R., et al., "Phase I Study of Single-agent Anti-programmed Death-1 (MDX-1106) in Refractory Solid Tumors: Safety, Clinical Activity, Pharmacodynamics, and Immunologic Correlates," *Journal of Clinical Oncology* 28(19):3167-3175, American Society of Clinical Oncology, United States (2010).

Condeelis, J. and Weissleder, R., "In Vivo Imaging in Cancer," Cold Spring Harbor Perspectives in Biology 2(12):a003848, Cold Spring Harbor Laboratory Press, United States (2010).

Drake, C.G., et al., "Safety, durable clinical benefit, and remission resulting from nivolumanb (Anti-PD-1; BMS-936558; ONO-4538) in a phase 1 trial in patients with previously treated metastatic renal cell carcinoma (mRCC); long-term patient follow-up," Abstracts of the 12th International Kidney Cancer Symposium. Oct. 25-26, 2013. Chicago, Illinois, USA, BJU International 112(Suppl.3):9, BJU International, England (2013).

(Continued)

*Primary Examiner* — Peter J Reddig
*Assistant Examiner* — Cheng Lu
(74) *Attorney, Agent, or Firm* — Sterne, Kessler, Goldstein & Fox P.L.L.C.

(57) ABSTRACT

This invention provides methods for treating cancer in a subject comprising administering to the subject an anti-PD-1 antibody and an anti-CD27 antibody. In some embodiments, the cancer is colorectal cancer, rectal cancer, colon cancer, lung cancer, melanoma, ovarian cancer, head and neck cancer, or any combination thereof.

18 Claims, 7 Drawing Sheets

(56) References Cited

U.S. PATENT DOCUMENTS

| | | | |
|---|---|---|---|
| 9,402,899 B2 | 8/2016 | Honjo et al. | |
| 9,439,962 B2 | 9/2016 | Honjo et al. | |
| 9,492,539 B2 | 11/2016 | Korman et al. | |
| 9,492,540 B2 | 11/2016 | Korman et al. | |
| 10,392,442 B2* | 8/2019 | Coric | C07K 16/3023 |
| 10,668,152 B2* | 6/2020 | Coric | A61K 39/001129 |
| 2006/0110383 A1 | 5/2006 | Honjo et al. | |
| 2009/0217401 A1 | 8/2009 | Korman et al. | |
| 2009/0297518 A1 | 12/2009 | Honjo et al. | |
| 2011/0081341 A1 | 4/2011 | Honjo et al. | |
| 2013/0017199 A1 | 1/2013 | Langermann | |
| 2013/0133091 A1 | 5/2013 | Korman et al. | |
| 2013/0309250 A1 | 11/2013 | Cogswell et al. | |
| 2014/0212422 A1 | 7/2014 | Korman et al. | |
| 2014/0294852 A1 | 10/2014 | Korman et al. | |
| 2014/0314714 A1 | 10/2014 | Honjo et al. | |
| 2014/0328833 A1 | 11/2014 | Korman et al. | |
| 2014/0348743 A1 | 11/2014 | Korman et al. | |
| 2015/0079109 A1 | 3/2015 | Li et al. | |
| 2015/0093380 A1 | 4/2015 | Honjo et al. | |
| 2015/0125463 A1 | 5/2015 | Cogswell et al. | |
| 2015/0165025 A1 | 6/2015 | Korman et al. | |
| 2015/0197572 A1 | 7/2015 | Honjo et al. | |
| 2016/0075782 A1 | 3/2016 | Korman et al. | |
| 2016/0090417 A1 | 3/2016 | Cogswell et al. | |
| 2016/0158355 A1 | 6/2016 | Honjo et al. | |
| 2016/0158356 A1 | 6/2016 | Honjo et al. | |
| 2016/0362495 A1 | 12/2016 | Korman et al. | |
| 2017/0051060 A1 | 2/2017 | Honjo et al. | |
| 2017/0088615 A1 | 3/2017 | Korman | |
| 2017/0143827 A1 | 5/2017 | Sadineni et al. | |
| 2017/0174774 A1 | 6/2017 | Coric et al. | |
| 2019/0153100 A1 | 5/2019 | Axelson et al. | |
| 2020/0024355 A1 | 1/2020 | Coric et al. | |

FOREIGN PATENT DOCUMENTS

| | | |
|---|---|---|
| WO | WO-2007005874 A2 | 1/2007 |
| WO | WO-2010019570 A2 | 2/2010 |
| WO | WO-2012145493 A1 | 10/2012 |
| WO | WO-2013173223 A1 | 11/2013 |
| WO | WO-2014179664 A2 | 11/2014 |
| WO | WO-2014194302 A2 | 12/2014 |
| WO | WO-2015042246 A1 | 3/2015 |
| WO | WO-2015085847 A1 | 6/2015 |
| WO | WO-2015112800 A1 | 7/2015 |
| WO | WO-2015112900 A1 | 7/2015 |
| WO | WO-2016149201 A2 | 9/2016 |
| WO | WO-2016168716 A1 | 10/2016 |

OTHER PUBLICATIONS

GenBank, "CD27 molecule [*Homo sapiens*]," Accession No. AAH12160.1, Nov. 7, 2006, accessed at https://www.ncbi.nlm.nih.gov/protein/AAH12160, accessed on Feb. 14, 2017, 3 pages.

GenBank, "Human hPD-1 (hPD-1) mRNA, complete cds," Accession No. U64863.1, Oct. 12, 2005, accessed at https://www.ncbi.nlm.nih.gov/nuccore/U64863, accessed on Dec. 6, 2016, 3 pages.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, Nov. 2, 2016, accessed at https://www.ncbi.nlm.nih.gov/protein/Q9NZQ7, accessed on Dec. 6, 2016, 11 pages.

Hamid, O., and Carvajal, R.D., "Anti-programmed death-1 and Anti-programmed death-ligand 1 antibodies in cancer therapy," *Expert Opinion on Biological Therapy* 13(6):847-861, Informa UK, Ltd., England (2013).

Hamid, O., et al., "Safety and Tumor Responses with Lambrolizumab (Anti-PD-1) in Melanoma," *The New England Journal of Medicine* 369(2): 134-144, Massachusetts Medical Society, United States of America (2013).

Hanna, N., et al., "Randomized Phase III Trial of Pemetrexed Versus Docetaxel in Patients with Non-Small-Cell Lung Cancer Previously Treated with Chemotherapy," *Journal of Clinical Oncology* 22(9):1589-1597, American Society of Clinical Oncology, United States (2004).

He, L-Z., et al., "Agonist Anti-human CD27 Monoclonal Antibody Induces T Cell Activation and Tumor Immunity in Human CD27-Transgenic Mice," *Journal of Immunology* 191(8):4174-4183, American Association of Immunologists, United States (2013).

Hodi, F.S., et al., "Improved Survival with Ipilimumab in Patients with Metastatic Melanoma," *The New England Journal of Medicine* 363(8):711-723, Massachusetts Medical Society, United States (2010).

Mccabe, K.E. and Wu, A.M., "Positive Progress in ImmunoPET—Not Just a Coincidence," *Cancer Biotherapy & Radiopharmaceuticals* 25(3):253-261, Mary Ann Liebert, Inc., United States (2010).

Mcdermott D.F., and Atkins, M.B., "PD-1 as a Potential Target in Cancer Therapy," *Cancer Medicine* 2(5):662-673, John Wiley & Sons Ltd., United States (2013).

National Cancer Institute, "Colorectal Cancer," cancer.gov, accessed at http://www.cancer.gov/types/colorectal, accessed on Feb. 14, 2017, 6 pages.

National Cancer Institute, Head and Neck Cancers, cancer.gov, accessed at https://www.cancer.gov/types/head-and-neck/head-neck-fact-sheet, accessed on Feb. 14, 2017, 13 pages.

National Cancer Institute, Ovarian Epithelial, Fallopian Tube, and Primary Peritoneal Cancer Treatment (PDQ®), cancer.gov, accessed at https://www.cancer.gov/types/ovarian/patient/ovarian-epithelial-treatment-pdq, accessed on Feb. 14, 2017, 22 pages.

National Cancer Institute, Skin Cancer (Including Melanoma), cancer.gov, accessed at http://www.cancer.gov/types/skin, accessed on Feb. 14, 2017, 6 pages.

National Comprehensive Cancer Network, "NCCN Guidelines," nccn.org, accessed at http://www.nccn.org/professionals/physiciangls/f guidelines.asp#site, accessed on Dec. 8, 2016, 4 pages.

NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.

NCI Drug Dictionary, "anti-PD-1 monoclonal antibody MEDI0680," cancer.gov, accessed at https://www.cancer.gov/publications/dictionaries/cancer-drug?cdrid=756047, accessed on Dec. 1, 2016, 3 pages.

NCI Drug Dictionary, "pembrolizumab," cancer.gov, accessed at https://www.cancer.gov/drugdictionary?cancer-drug?cdrid=695789, accessed on Dec. 1, 2016, 3 pages.

Olafsen, T., et al., "ImmunoPET imaging of B-Cell Lymphoma Using $^{124}$I-Anti-CD20 scFv Dimers (Diabodies)," *Protein Engineering, Design & Selection* 23(4):243-249, Oxford University Press, England (2010).

Pawlik, T.M., et al., "Colorectal Carcinogenesis: MSI-H Versus MSI-L," *Disease Markers* 20(4-5):199-206, IOS Press and the authors, United States (2004).

Siegel, R., et al., "Cancer Statistics, 2014," *CA: A Cancer Journal for Clinicians* 64(1):9-29, American Cancer Society, United States (Jan. 7, 2014).

Sjoblom, T., et al., "The Consensus Coding Sequences of Human Breast and Colorectal Cancers," *Science* 314(5797):268-274, American Association for the Advancement of Science, United States (2006).

Taube, J.M., et al., "Colocalization of Inflammatory Response With B7-H1 Expression in Human Melanocytic Lesions Supports an Adaptive Resistance Mechanism of Immune Escape," *Science Translational Medicine* 4(127):127ra37, American Association for the Advancement of Science, United States (2012).

Thomas, L.J., et al., "Targeting Human CD27 with an Agonist Antibody Stimulates T-cell Activation and Antitumor Immunity," *OncoImmunology* 3(1):e27255, Landes Bioscience, United States, 3 pages (Jan. 1, 2014).

Topalian, S.L., et al., "Safety, Activity, and Immune Correlates of Anti-PD-1 Antibody in Cancer," *The New England Journal of Medicine* 366(26):2443-2454, Massachusetts Medical Society, United States (2012).

Topalian, S.L., et al., "Targeting the PD-1/B7-H1(PD-L1) Pathway to Activate Anti-tumor Immunity," *Current Opinion in Immunology* 24(2):207-212, Elsevier Ltd., England (2012).

(56) References Cited

OTHER PUBLICATIONS

Topalian, S.L., et al., "Survival, Durable Tumor Remission, and Long-term Safety in Patients with Advanced Melanoma Receiving Nivolumab," *Journal of Clinical Oncology* 32(10): 1020-1030, American Society of Clinical Oncology, United States (Mar. 3, 2014).

United States Adopted Name (USAN) Drug Finder, "Pembrolizumab: Statement on a nonproprietary name adopted by the USAN Council (ZZ-165)," published Nov. 27, 2013, accessed at https://searchusan.ama-assn.org/usan/document Download?uri=%2Funstructured%2Fbinary%2Fusan%2Fpembrolizum ab.pdf, accessed on Dec. 8, 2016, 2 pages.

Vitale, L.A., et al., "Development of a Human Monoclonal Antibody for Potential Therapy of CD27-Expressing Lymphoma and Leukemia," *Clinical Cancer Research* 18(14):3812-3821, The Association, United States (2012).

Wang, C., et al., "In Vitro Characterization of the Anti-PD-1 Antibody Nivolumab, BMS-936558, and In Vivo Toxicology in Non-Human Primates," Cancer Immunology Research 2(9):846-856, American Association for Cancer Research, United States (May 28, 2014).

National Comprehensive Cancer Network, "NCCN Clinical Practice Guidelines in Oncology Non-Small Cell Lung Cancer Version 3.2014," nccn.org, accessed at http://www.24hmb.com/voimages/web_image//upload/file/20140416/28501397633488076.pdf, accessed on Feb. 21, 2017, 148 pages.

Non-Final Office Action dated Mar. 16, 2020, in co-pending U.S. Appl. No. 16/505,288, to Coric et al., filed Jul. 8, 2019, 7 pages.

Office Action dated Sep. 26, 2018, in U.S. Appl. No. 15/384,205, inventor Coric; V., et al., filed Dec. 19, 2016, 5 pages.

Office Action dated May 31, 2019, in U.S. Appl. No. 15/613,192, inventor Coric; V., et al., filed Jun. 3, 2017, 7 pages.

Office Action dated Jul. 14, 2020, in U.S. Appl. No. 16/505,288, inventor Coric; V., et al., filed Jul. 8, 2019, 6 pages.

\* cited by examiner

USE OF ANTI-PD-1 ANTIBODY IN COMBINATION WITH ANTI-CD27 ANTIBODY IN CANCER TREATMENT

CROSS-REFERENCE TO RELATED APPLICATIONS

This application is a continuation of U.S. application Ser. No. 16/505,288 filed on Jul. 8, 2019, which is a continuation of U.S. application Ser. No. 15/384,205 filed on Dec. 19, 2016, issued as U.S. Pat. No. 10,392,442, which claims benefit to U.S. Provisional Application No. 62/268,990, filed Dec. 17, 2015, each of which is incorporated herein by reference in its entirety.

FIELD OF THE INVENTION

This invention relates to methods for treating cancer in a subject comprising administering to the subject an anti-Programmed Death-1 (PD-1) antibody and an anti-CD27 antibody. In some embodiments, the cancer is colorectal cancer, rectal cancer, colon cancer, lung cancer, melanoma, ovarian cancer, head and neck cancer, or any combination thereof.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Until recently, cancer immunotherapy had focused substantial effort on approaches that enhance anti-tumor immune responses by adoptive-transfer of activated effector cells, immunization against relevant antigens, or providing non-specific immune-stimulatory agents such as cytokines. In the past decade, however, intensive efforts to develop specific immune checkpoint pathway inhibitors have begun to provide new immunotherapeutic approaches for treating cancer, including the development of an antibody (Ab), ipilimumab (YERVOY®), that binds to and inhibits CTLA-4 for the treatment of patients with advanced melanoma (Hodi et al., 2010) and the development of antibodies such as nivolumab and pembrolizumab (formerly lambrolizumab; USAN Council Statement, 2013) that bind specifically to the Programmed Death-1 (PD-1) receptor and block the inhibitory PD-1/PD-1 ligand pathway (Topalian et al., *N Engl J Med* 366:2443-54 (2012a); Topalian et al., *Curr Opin Immunol* 24:207-12 (2012b); Topalian et al., *J Clin Oncol* 32(10):1020-30 (2014); Hamid et al., *N Engl J Med* 369: 134-144 (2013); Hamid and Carvajal, *Expert Opin Biol Ther* 13(6):847-61 (2013); McDermott and Atkins, *Cancer Med* 2(5): 662-73(2013)).

Targeted therapy of multiple non-redundant molecular pathways regulating immune responses may enhance antitumor immunotherapy. However, not all combinations have acceptable therapies. There remains a need for combination therapies with an acceptable safety profile and high efficacy that enhance antitumor immune responses compared to monotherapy and other immunotherapy combinations.

SUMMARY OF THE INVENTION

The present invention relates to a method for treating a subject afflicted with cancer, e.g., a tumor, comprising administering to the subject: (a) an antibody or an antigen-binding portion thereof that binds specifically to a Programmed Death-1 (PD-1) receptor and inhibits PD-1 activity ("anti-PD-1 antibody"); and (b) an antibody or an antigen-binding portion thereof that specifically binds to CD27 ("anti-CD27 antibody").

In certain embodiments, the cancer, e.g., a tumor, is colorectal cancer, rectal cancer, colon cancer, lung cancer, melanoma, ovarian cancer, head and neck cancer, or any combination thereof. In certain embodiments, the lung cancer is non-small cell lung cancer (NSCLC). In one embodiment, the NSCLC has a squamous histology. In another embodiment, the NSCLC has a non-squamous histology. In one embodiment, the administering treats the cancer.

In some embodiments, the anti-PD-1 antibody cross-competes with nivolumab for binding to human PD-1. In one embodiment, the anti-PD-1 antibody binds to the same epitope as nivolumab. In certain embodiments, the anti-PD-1 antibody is a chimeric, humanized or human monoclonal antibody or a portion thereof. In other embodiments, the anti-PD-1 antibody comprises a heavy chain constant region which is of a human IgG1 or IgG4 isotype. In one embodiment, the anti-PD-1 antibody is nivolumab. In another embodiment, the anti-PD-1 antibody is pembrolizumab.

In certain embodiments, the anti-PD-1 antibody is administered at a dose ranging from at least about 0.1 to at least about 10.0 mg/kg body weight once about every 1, 2 or 3 weeks. In one embodiment, the anti-PD-1 antibody is administered at a dose of at least about 3 mg/kg body weight once about every 2 weeks. In other embodiments, the anti-PD-1 antibody is administered for as long as clinical benefit is observed or until unmanageable toxicity or disease progression occurs.

In certain embodiments, the anti-CD27 antibody cross-competes with varlilumab for binding to human CD27. In one embodiment, the anti-CD27 antibody binds to the same epitope as varlilumab. In certain embodiments, the anti-CD27 antibody is a chimeric, humanized or human monoclonal antibody or a portion thereof. In certain embodiments, the anti-CD27 antibody comprises a heavy chain constant region which is of a human IgG1 or IgG4 isotype. In one embodiment, the anti-CD27 antibody is varlilumab.

In certain embodiments, the anti-CD27 antibody is administered at a dose ranging from at least about 0.01 to at least about 10 mg/kg body weight once about every 1, 2 or 3 weeks. In one embodiment, the anti-CD27 antibody is administered at a dose of at least about 0.1 mg/kg body weight once about every 2 weeks. In another embodiment, the anti-CD27 antibody is administered at a dose of at least about 1 mg/kg body weight once about every 2 weeks. In yet another embodiment, the anti-CD27 antibody is administered at a dose of at least about 10 mg/kg body weight once about every 2 weeks. In other embodiments, the anti-CD27 antibody is administered for as long as clinical benefit is observed or until unmanageable toxicity or disease progression occurs.

In some embodiments, the anti-PD-1 and anti-CD27 antibodies are formulated for intravenous administration. In certain embodiments, the anti-PD-1 and anti-CD27 antibodies are administered sequentially. In one embodiment, the anti-PD-1 and anti-CD27 antibodies are administered within 30 minutes of each other. In an embodiment, the anti-PD-1 antibody is administered before the anti-CD27 antibody. In another embodiment, the anti CD27 antibody is administered before the anti-PD-1 antibody. In certain embodiments, the anti-PD-1 antibody and the anti-CD27 antibody are administered concurrently in separate compositions. In other embodiments, the anti-PD-1 antibody and the anti-CD27 antibody are admixed as a single composition for concurrent administration.

In one embodiment, the anti-PD-1 antibody is administered at a subtherapeutic dose. In another embodiment, the anti-CD27 antibody is administered at a subtherapeutic dose. In a further embodiment, the anti-PD-1 antibody and the anti-CD27 antibody are each administered at a subtherapeutic dose.

In certain embodiments, the subject has a tumor that expresses PD-L1, PD-L2, or both. In embodiments, the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

The present invention also relates to kit for treating a subject afflicted with a cancer, the kit comprising: (a) a dosage ranging from about 4 mg to about 500 mg of an anti-PD-1 antibody; (b) a dosage ranging from about 0.4 mg to about 500 mg of an anti-CD27 antibody; and (c) instructions for using the anti-PD-1 antibody and the anti-CD27 antibody in any method disclosed herein.

In some embodiments, the subject has a microsatellite stable (MSS) tumor or a microsatellite instability low (MSI-L) tumor. Certain embodiments further comprise measuring the microsatellite status of a tumor prior to the administration. In certain embodiments, the tumor is a MSS tumor or a MSI-L tumor. In one embodiment, the subject is afflicted with a colon cancer, e.g., the tumor is colon cancer.

EMBODIMENTS

E1. A method for treating a subject afflicted with cancer comprising administering to the subject:
(a) an antibody or an antigen-binding portion thereof that binds specifically to a Programmed Death-1 (PD-1) receptor and inhibits PD-1 activity ("anti-PD-1 antibody"); and
(b) an antibody or an antigen-binding portion thereof that specifically binds to CD27 ("anti-CD27 antibody").

E2. The method of embodiment E1, wherein the cancer is colorectal cancer, rectal cancer, colon cancer, lung cancer, melanoma, ovarian cancer, head and neck cancer, or any combination thereof.

E3. The method of embodiment E2, wherein the lung cancer is non-small cell lung cancer (NSCLC).

E4. The method of embodiment E3, wherein the NSCLC has a squamous histology.

E5. The method of embodiment E3, wherein the NSCLC has a non-squamous histology.

E6. The method of any one of embodiments E1 to E5, wherein the administering treats the cancer.

E7. The method of any one of embodiments E1 to E6, wherein the anti-PD-1 antibody or the antigen-binding portion thereof cross-competes with nivolumab for binding to human PD-1.

E8. The method of any one of embodiments E1 to E7, wherein the anti-PD-1 antibody or the antigen-binding portion thereof binds to the same epitope as nivolumab.

E9. The method of any one of embodiments E1 to E8, wherein the anti-PD-1 antibody is a chimeric, humanized or human monoclonal antibody.

E10. The method of any one of embodiments E1 to E9, wherein the anti-PD-1 antibody comprises a heavy chain constant region which is of a human IgG1 or IgG4 isotype.

E11. The method of any one of embodiments E1 to E10, wherein the anti-PD-1 antibody is nivolumab.

E12. The method of any one of embodiments E1 to E10, wherein the anti-PD-1 antibody is pembrolizumab.

E13. The method of any one of embodiments E1 to E12, wherein the anti-PD-1 antibody is administered at a dose ranging from at least about 0.1 to at least about 10.0 mg/kg body weight once about every 1, 2 or 3 weeks.

E14. The method of embodiment E13, wherein the anti-PD-1 antibody is administered at a dose of at least about 3 mg/kg body weight once about every 2 weeks.

E15. The method of any one of embodiments E1 to E14, wherein the anti-PD-1 antibody is administered for as long as clinical benefit is observed or until unmanageable toxicity or disease progression occurs.

E16. The method of any one of embodiments E1 to E15, wherein the anti-CD27 antibody or the antigen-binding portion thereof cross-competes with varlilumab for binding to human CD27.

E17. The method of any one of embodiments E1 to E16, wherein the anti-CD27 antibody or the antigen-binding portion thereof binds to the same epitope as varlilumab.

E18. The method of any one of embodiments E1 to E17, wherein the anti-CD27 antibody is a chimeric, humanized or human monoclonal antibody.

E19. The method of any one of embodiments E1 to E18, wherein the anti-CD27 antibody comprises a heavy chain constant region which is of a human IgG1 or IgG4 isotype.

E20. The method of any one of embodiments E1 to E19, wherein the anti-CD27 antibody is varlilumab.

E21. The method of any one of embodiments E1 to E20, wherein the anti-CD27 antibody is administered at a dose ranging from at least about 0.01 to at least about 10 mg/kg body weight once about every 1, 2 or 3 weeks.

E22. The method of embodiment E21, wherein the anti-CD27 antibody is administered at a dose of at least about 0.1 mg/kg body weight once about every 2 weeks.

E23. The method of embodiment E21, wherein the anti-CD27 antibody is administered at a dose of at least about 1 mg/kg body weight once about every 2 weeks.

E24. The method of embodiment E21, wherein the anti-CD27 antibody is administered at a dose of at least about 10 mg/kg body weight once about every 2 weeks.

E25. The method of any of embodiments E1 to E24, wherein the anti-CD27 antibody is administered for as long as clinical benefit is observed or until unmanageable toxicity or disease progression occurs.

E26. The method of any one of embodiments E1 to E25, wherein the anti-PD-1 and anti-CD27 antibodies are formulated for intravenous administration.

E27. The method of any one of embodiments E1 to E26, wherein the anti-PD-1 and anti-CD27 antibodies are administered sequentially.

E28. The method of any one of embodiments E1 to E27, wherein the anti-PD-1 and anti-CD27 antibodies are administered within 30 minutes of each other.

E29. The method of any one of embodiments E1 to E28, wherein the anti-PD-1 antibody is administered before the anti-CD27 antibody.

E30. The method of any one of embodiments E1 to E28, wherein the anti CD27 antibody is administered before the anti-PD-1 antibody.

E31. The method of any one of embodiments E1 to E26, wherein the anti-PD-1 antibody and the anti-CD27 antibody are administered concurrently in separate compositions.

E32. The method of any one of embodiments E1 to E26, wherein the anti-PD-1 antibody and the anti-CD27 antibody are admixed as a single composition for concurrent administration.

E33. The method of any one of embodiments E1 to E32, wherein the anti-PD-1 antibody is administered at a subtherapeutic dose.

E34. The method any one of embodiments E1 to E33, wherein the anti-CD27 antibody is administered at a subtherapeutic dose.

E35. The method any one of embodiments E1 to E34, wherein the anti-PD-1 antibody and the anti-CD27 antibody are each administered at a subtherapeutic dose.

E36. The method of any one of embodiments E1 to E35, wherein the subject has a tumor that expresses PD-L1, PD-L2, or both.

E37. The method of any one of embodiments E1 to E36, wherein the subject exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the initial administration.

E38. A kit for treating a subject afflicted with a cancer, the kit comprising:
 (a) a dosage ranging from about 4 mg to about 500 mg of an anti-PD-1 antibody;
 (b) a dosage ranging from about 0.4 mg to about 500 mg of an anti-CD27 antibody; and
 (c) instructions for using the anti-PD-1 antibody and the anti-CD27 antibody in the method of any one of embodiments E1 to E37.

E39. The method of any one of embodiments E1 to E37, wherein the subject is afflicted with a colon cancer.

E40. The method of embodiment E39, wherein the subject has a microsatellite stable (MSS) tumor or a microsatellite instability low (MSI-L) tumor.

E41. The method of embodiment E39, further comprising measuring the microsatellite status of a tumor prior to the administration.

E42. The method of embodiment E39, wherein the tumor is a MSS tumor or a MSI-L tumor.

DETAILED DESCRIPTION OF THE INVENTION

Figure 1:
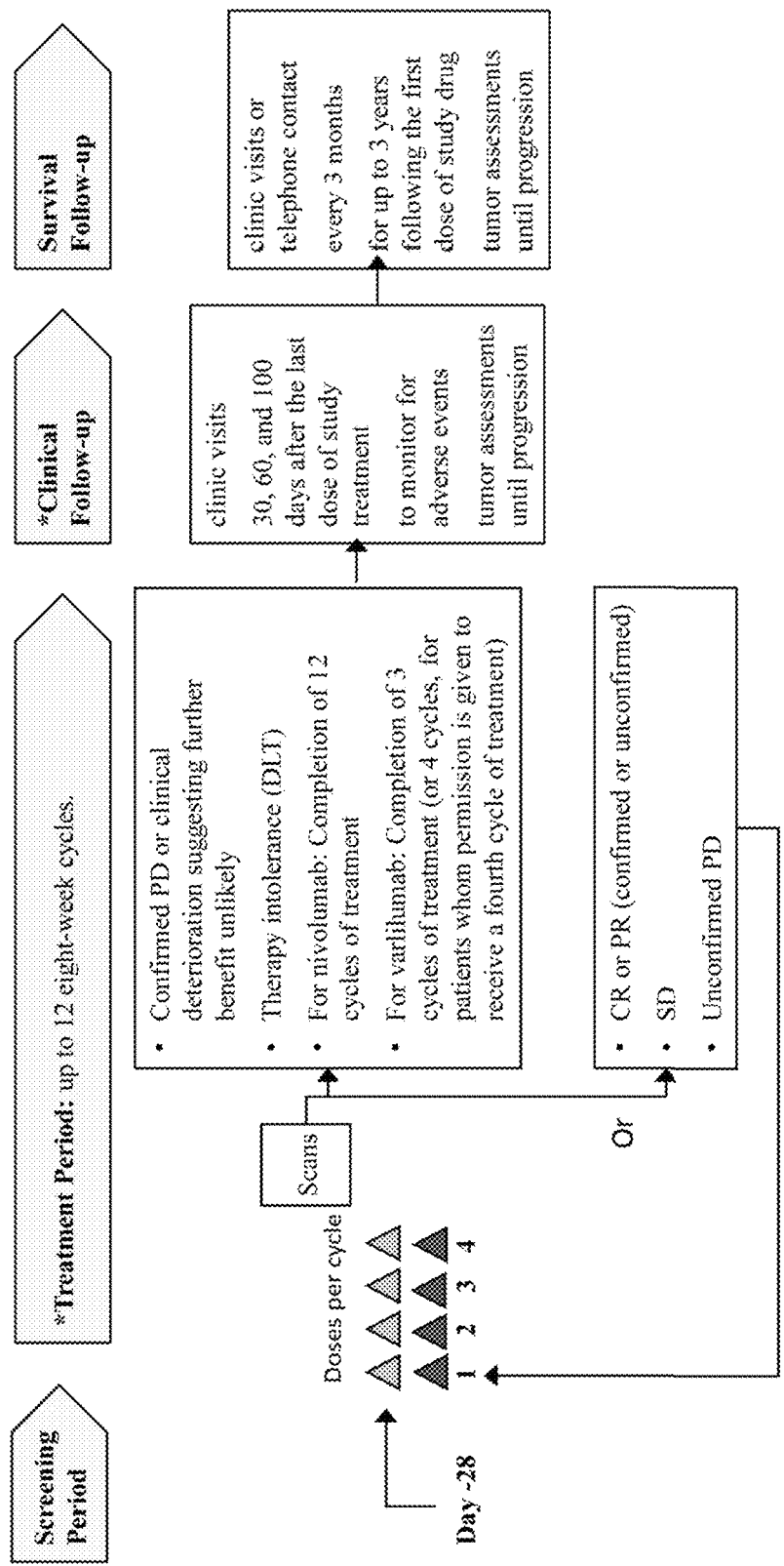
FIG. 1 shows the study schema and schedule of assessments for a Phase I/II clinical trial of varlilumab in combination with nivolumab.

This invention relates to methods for treating cancer in a subject comprising administering to the subject an anti-Programmed Death-1 (PD-1) antibody and an anti-CD27 antibody. In some embodiments, the cancer is colorectal cancer, rectal cancer, colon cancer, lung cancer, melanoma, ovarian cancer, head and neck cancer, or any combination thereof.

Terms

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a therapeutic agent to a subject, using any of the various methods and delivery systems known to those skilled in the art. Exemplary routes of administration for the anti-PD-1 antibody include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent may be administered via a non-parenteral route, or orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 may, however, have cross-reactivity to other antigens, such as PD-1 molecules from different species. Moreover, an isolated antibody may be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A monoclonal antibody is an example of an isolated antibody. Monoclonal antibodies may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CD27 antibody binds specifically to CD27.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream. In some embodiments, the cancer is colorectal cancer, rectal cancer, colon cancer, lung cancer, melanoma, ovarian cancer, head and neck cancer, or any combination thereof. In certain embodiments, the lung cancer is non-small cell lung cancer (NSCLC). In embodiments, the NSCLC has a squamous histology. In other embodiments, the NSCLC has a nonsquamous histology. A "cancer" or "cancerous tissue" can include a tumor. A "tumor" refers to all neoplastic cell growth and proliferation, whether malignant or benign, and all pre-cancerous and cancerous cells and tissues.

"CD27" refers to a receptor that is a member of the tumor necrosis factor receptor superfamily. CD27 is required for generation and long-term maintenance of T cell immunity, and binds to CD70. CD27 is constitutively expressed on the majority of mature T cells, memory B cells, and a portion of natural killer cells. The interaction of CD27 with its ligand CD70 plays key roles in the following processes: 1) costimulation through CD27 on T cells causes activation, proliferation, survival, and maturation of effector capacity and memory; 2) costimulation through CD27 on human B cells activates and promotes the generation of plasma cells, proliferation, and the production of immunoglobulin and 3) costimulation through CD27 on natural killer cells induces cytolytic activity. The term "CD27" as used herein includes human CD27 (hCD27), variants, isoforms, and species homologs of hCD27, and analogs having at least one common epitope with hCD27. The complete hCD27 sequence can be found under GenBank Accession No. AAH12160. The expression of CD27 on various types of lymphomas and leukemias such as Chronic Lymphocytic Leukemia, Mantle Cell Lymphoma, Primary Central Nervous System Lymphoma, Burkitt's Lymphoma, and Marginal Zone B cell Lymphoma has been well documented.

The term "immunotherapy" refers to the treatment of a subject afflicted with, or at risk of contracting or suffering a recurrence of, a disease by a method comprising inducing, enhancing, suppressing or otherwise modifying an immune response.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that down regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

As used herein, "subtherapeutic dose" means a dose of a therapeutic compound (e.g., an antibody) that is lower than the usual or typical dose of the therapeutic compound when administered alone for the treatment of a hyperproliferative disease (e.g., cancer).

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent inhibits cell growth or tumor growth by at least about 20%, by at least about 30%, by at least about 40%, by at least about 50%, by at least about 60%, by at least about 70%, or by at least about 80% relative to untreated subjects.

In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "weight based dose" as referred to herein means that a dose that is administered to a patient is calculated based on the weight of the patient. For example, when a patient with 60 kg body weight requires 3 mg/kg of an anti-PD-1 antibody, one can calculate and use the appropriate amount of the anti-PD-1 antibody (i.e., 180 mg) for administration.

The use of the term "fixed dose" with regard to a method of the invention means that two or more different antibodies in a single composition (e.g., anti-PD-1 antibody and anti-CD27 antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-PD-1 antibody) to mg second antibody (e.g., anti-CD27 antibody). For example, the 3:1 ratio of an anti-PD-1 antibody and an anti-CD27 antibody can mean that a vial can contain about 240 mg of the anti-PD-1 antibody and 80 mg of the anti-CD27 antibody or about 3 mg/ml of the anti-PD-1 antibody and 1 mg/ml of the anti-CD27 antibody.

The use of the term "flat dose" with regard to the methods and dosages of the invention means a dose that is administered to a patient without regard for the weight or body surface area (BSA) of the patient. The flat dose is therefore not provided as a mg/kg dose, but rather as an absolute amount of the agent (e.g., the anti-CD27 antibody and/or anti-PD-1 antibody). For example, a 60 kg person and a 100 kg person would receive the same dose of an antibody (e.g., 240 mg of an anti-PD1 antibody).

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days ±one day, i.e., every six days to every eight days. "Once about every two weeks" can include every fourteen days ±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Methods of the Invention

The present invention is directed to a method for treating a cancer or a subject afflicted with cancer comprises administering to the subject a therapeutically effective amount of an antibody or an antigen-binding portion thereof that binds specifically to a Programmed Death-1 (PD-1) receptor and inhibits PD-1 activity ("anti-PD-1 antibody") and a therapeutically effective amount of an antibody or an antigen-binding portion thereof that binds specifically to CD27 ("anti-CD27 antibody").

In some embodiments, the cancer is colorectal cancer, rectal cancer, colon cancer, lung cancer, melanoma, ovarian cancer, head and neck cancer, or any combination thereof. In certain embodiments, the subject has received one, two, three, four, five or more prior cancer treatments. In other embodiments, the subject is treatment-naïve. In some embodiments, the subject has progressed on other cancer treatments. In embodiments, the cancer has reoccurred. In some embodiments, the cancer is metastatic. In other embodiments, the cancer is not metastatic.

In certain embodiments, the lung cancer is non-small cell lung cancer (NSCLC). In embodiments, the NSCLC has a squamous histology. In other embodiments, the NSCLC has a nonsquamous histology. In yet other embodiments, the NSCLC has a squamous adenosquamous histology. In further embodiments, the NSCLC has a histology that is not otherwise specified. In certain embodiments, the malignancy is unresectable. In some embodiments, the NSCLC EGFR mutated.

In some embodiments, the head and neck cancer is recurrent or metastatic or recurrent SCCHN (oral cavity, pharynx, larynx). In certain embodiments the head and neck cancer is stage III/IV. In some embodiments, the cancer has progressed or reoccurred within six months of the last dose of platinum therapy. In embodiments, the cancer is therapy-refractory.

In embodiments, the ovarian cancer is recurrent or persistent epithelial ovarian, fallopian tube or primary peritoneal carcinoma. In embodiments, the subjects received a platinum-taxane based chemotherapy regimen as their frontline therapy for ovarian cancer.

In some embodiments, the colorectal cancer is histologically confirmed. In certain embodiments, the colorectal cancer is metastatic or recurrent. In embodiments, the subject has had progression during, after, or been intolerant following the last administration of standard therapies. In certain embodiments, the subject has microsatellite instability. In other embodiments, the colorectal cancer has low microsatellite instability (MSI-L).

In certain embodiments, the melanoma is advance disease (previously treated, therapy-refractory or recurrent Stage III (unresectable) or Stage IV). In embodiments, the patient with melanoma has a known BRAF V600 mutation. In certain embodiments, the patient has melanoma that is no longer controlled by surgery, chemotherapy or radiotherapy. In embodiments, the patient has melanoma that is refractory to or relapsed after surgery. In other embodiments, the patient is treatment-naïve.

In other embodiments, the present methods comprise administering an effective amount of an anti-PD-1 antibody and an effective amount of an anti-CD27 antibody. An effective amount of an anti-PD-1 antibody and/or an anti-CD27 antibody can be a flat dose or a weight based dose.

In certain embodiments, the therapy of the present invention (e.g., administration of an anti-PD-1 antibody the anti-CD27 antibody) effectively increases the duration of survival of the subject. For example, the duration of survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year or more when compared to another subject treated with only either another therapy or, only one of the two members of the combination therapy alone (e.g., an anti-PD-1 antibody alone) or an alternative combination therapy. In other embodiments, the combination therapy of an anti-PD-1 antibody and an anti-CD27 antibody increases the duration of survival of the subject at a level similar to the duration of survival of the subject using a combination therapy of an anti-PD-L1 antibody and varlilumab (anti-CD27 antibody). In still other embodiments, the combination therapy of an anti-PD-1 antibody (e.g., nivolumab) and an anti-CD27 antibody (e.g., varlilumab) increases the duration of survival of the subject at a level higher than (about one month higher than, about two months higher than, about three months higher than, about four months higher than, about five months higher than, about six months higher than, about seven months higher than, about eight months higher than, about nine months higher than, about ten months higher than, about eleven months higher than, or about one year higher than the duration of survival of the subject using a combination therapy of an anti-PD-L1 antibody (e.g., atezolizumab, i.e., MPDL3280A) and varlilumab (anti-CD27 antibody). In certain embodiments, the therapy of the present invention effectively increases the duration of progression-free survival of the subject. For example, the progression free survival of the subject is increased by at least about 1 month, at least about 2 months, at least about 3 months, at least about 4 months, at least about 5 months, at least about 6 months, at least about 7 months, at least about 8 months, at least about 9 months, at least about 10 months, at least about 11 months or at least about 1 year when compared to another subject treated with only either another therapy or only one of the two members of the combination therapy alone (e.g., an anti-PD-1 antibody alone) or an alternative combination therapy. In certain embodiments, the therapy of the present invention effectively increases the response rate in a group of subjects. For example, the response rate in a group of subjects is increased by at least about 2%, at least about 3%, at least about 4%, at least about 5%, at least about 10%, at least about 15%, at least about 20%, at least about 25%, at least about 30%, at last about 35%, at least about 40%, at least about 45%, at least about 50%, at least about 55%, at least about 60%, at least about 70%, at least about 75%, at least about 80%, at least about 85%, at least about 90%, at least about 95%, at least about 99% or at least about 100% when compared to another group of subjects treated with only either another therapy or, only one of the two members of the combination therapy alone (e.g., an anti-PD-1 antibody alone) or an alternative combination therapy.

In some embodiments, the anti-PD-1 and anti-CD27 antibodies are formulated for intravenous administration. In certain embodiments, the anti-PD-1 and anti-CD27 antibodies are administered sequentially. In embodiments, the anti-PD-1 and anti-CD27 antibodies are administered within 30 minutes of each other. In one embodiment, the anti-PD-1 antibody is administered before the anti-CD27 antibody. In another embodiment, the anti CD27 antibody is administered before the anti-PD-1 antibody. In another embodiment, the anti-PD-1 antibody and the anti-CD27 antibody are administered concurrently in separate compositions. In a further embodiment, the anti-PD-1 antibody and the anti-CD27 antibody are admixed as a single composition for concurrent administration.

In some embodiments, the anti-PD-1 antibody and anti-CD27 antibody are administered in a fixed dose.

In embodiments, the cancer is microsatellite stable (MSS) (or "MSI stable") and therefore has no microsatellite instability.

Microsatellite instability is the condition of genetic hypermutability that results from impaired DNA mismatch repair (MMR). The presence of MSI represents phenotypic evidence that MMR is not functioning normally. In most cases, the genetic basis for instability in MSI tumors is an inherited germline alteration in any one of the five human MMR genes: MSH2, MLH1, MSH6, PMS2, and PMS1. In certain embodiments, the subject receiving tumor treatment has no instability (MSS or MSI stable) and has no mutation in genes MSH2, MLH1, MSH6, PMS2, and PMS1. The present invention is also directed to methods of treating a tumor, e.g., tumor in colon, comprising identifying a subject responsive to the combination therapy of an anti-PD-1 antibody and an anti-CD27 antibody, wherein the subject has a MSI stable or MSI low tumor. In other embodiments, the invention includes a method of treating a tumor, e.g., tumor in colon, comprising (i) identifying a subject who has a MSI stable or MSI low (MSI-L) tumor and (ii) administering an effective amount of an anti-PD-1 antibody and an effective amount of an anti-CD27 antibody to the subject. In some embodiments, the invention provides a method of treating a tumor, e.g., a tumor in colon, comprising (i) identifying a subject who has a tumor that is not a MSI-high (MSI-H) tumor and (ii) administering an effective amount of an anti-PD-1 antibody and an effective amount of an anti-CD27 antibody to the subject. As used herein, MSI-H tumors mean tumors having greater than at least about 30% of unstable MSI biomarkers. As used herein, MSI-L tumors mean tumors having less than about 10%, about 20%, or about 30% of unstable MSI biomarkers. In some embodiments, a colorectal cancer is MSI-L when a minority of tested biomarkers exhibit instability. In certain embodiments, the present invention is directed to a method of treating a cancer comprising 1) identifying the microsatellite status of a tumor and 2) administering a therapy to the subject based on the microsatellite status. In other embodiments, the subject has MSI-L. In embodiments, the patient is MSI stable. The PD-L1 status of a tumor in a subject can be measured prior to administering any composition or utilizing any method disclosed herein. PD-L1 expression can be determined by any methods known in the art.

In order to assess the PD-L1 expression, in one embodiment, a test tissue sample can be obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the anti-PD-1 antibody or anti-PD-L1 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FM), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, "In vivo imaging in cancer," *Cold Spring Harb. Perspect. Biol.* 2(12):a003848 (2010)). Antibody specificity, coupled with the sensitivity and resolution of PET, makes immunoPET imaging particularly attractive for monitoring and assaying expression of antigens in tissue samples (McCabe and Wu, "Positive progress in immunoPET—not just a coincidence," *Cancer Biother. Radiopharm.* 25(3):253-61 (2010); Olafsen et al., "ImmunoPET imaging of B-cell lymphoma using 124I-anti-CD20 scFv dimers (diabodies)," *Protein Eng. Des. Sel.* 23(4):243-9 (2010)). In certain embodiments of any of the present methods, PD-L1 expression is assayed by immunoPET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 monoclonal antibody to bind to the PD-L1 polypeptide.

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a monoclonal antibody that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary antibody; incubating with a post primary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1+ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%. In one embodiment, the threshold number of cells that needs to be PD-L1 positive is at least about 100, at least about 125, at least about 150, at least about 175, or at least about 200 cells. In certain embodiments, the threshold number or cells that needs to be PD-L1 positive is at least about 100 cells.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

Histoscore=[(% tumor×1(low intensity))+(% tumor× 2(medium intensity))+(% tumor×3(high intensity)]

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., "Colocalization of inflammatory response with B7-h1 expression in human melanocytic lesions supports an adaptive resistance mechanism of immune escape," *Sci. Transl. Med.* 4(127):127ra37 (2012)).

In one embodiment, the PD-L1 expression level of a tumor is at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100%. In another embodiment, the PD-L1 status of a tumor is at least about 1%. In other embodiments, the PD-L1 status of the subject is at least about 5%. In a certain embodiment, the PD-L1 status of a tumor is at least about 10%. In a one embodiment, the PD-L1 status of the tumor is at least about 25%. In a particular embodiment, the PD-L1 status of the tumor is at least about 50%.

In some embodiments, the present invention includes methods of treating a MSI-high (MSI-H) tumor, a MSI stable tumor, or a MSI low (MSI-L) tumor, e.g., a colorectal tumor, comprising administering the combination therapy of an anti-PD-1 antibody and an anti-CD27 antibody to a subject that has a tumor expressing PD-L1 or a PD-L1 positive tumor. In certain embodiments, the present invention is directed to a method of treating a tumor, e.g., a colorectal tumor, comprising (i) identifying a subject who has a MSI-high (MSI-H) tumor, a MSI stable tumor, or a MSI low (LSI-L) tumor; (ii) assessing whether the tumor expresses PD-L1; and (iii) administering an effective amount of an anti-PD-1 antibody and an effective amount of an anti-CD27 antibody to the subject. In certain embodiments, the subject has a tumor that has ≥1% PD-L1 expression, ≥5% PD-L1 expression, ≥10% PD-L1 expression, ≥25% PD-L1 expression, or ≥50% PD-L1 expression.

In another embodiment, the invention provides a method of treating a tumor, e.g., a colorectal tumor, comprising (i) identifying a subject who has a MSI-high (MSI-H) tumor, a MSI stable tumor, or a MSI low (LSI-L) tumor; (ii) assessing whether the tumor is PD-L1 positive; and (iii) administering an effective amount of an anti-PD-1 antibody and an effective amount of an anti-CD27 antibody to the subject.

"PD-L1 positive" as used herein can be interchangeably used with "PD-L1 expression of at least about 1%". In one embodiment, the PD-L1 positive tumors can thus have at least about 1%, at least about 2%, at least about 5%, at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%, or about 100% of the tumor cells expressing PD-L1 as measured by an automated IHC. In certain embodiments, "PD-L1 positive" means that there are at least 100 cells that express PD-L1 on the surface of the cells.

Anti-PD-1 Antibodies

The combination therapy of the present invention can utilize an anti-PD-1 antibody or an antigen-binding fragment thereof. PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

Human monoclonal antibodies that bind specifically to PD-1 with high affinity have been disclosed in U.S. Pat. No. 8,008,449. Other anti-PD-1 monoclonal antibodies have been described in, for example, U.S. Pat. Nos. 6,808,710, 7,488,802, 8,168,757 and 8,354,509, and PCT Publication No. WO 2012/145493. Each of the anti-PD-1 human monoclonal antibodies disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and/or (j) inhibits tumor cell growth in vivo. Anti-PD-1 antibodies usable in the present invention include monoclonal antibodies that bind specifically to human PD-1 and exhibit at least one, at least two, at least three, at least four or at least five of the preceding characteristics.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the downregulation of antitumor T-cell functions (U.S. Pat. No. 8,008,449; Wang et al., 2014 *Cancer Immunol Res.* 2(9): 846-56). Nivolumab has shown activity in a variety of advanced solid tumors including renal cell carcinoma (renal adenocarcinoma, or hypernephroma), melanoma, and non-small cell lung cancer (NSCLC) (Topalian et al., 2012a; Topalian et al., 2014; Drake et al., 2013; WO 2013/173223). In another embodiment, the anti-PD-1 antibody or fragment thereof cross-competes with nivolumab. In some embodiments, the anti-PD-1 antibody binds to the same epitope as nivolumab. In certain embodiments, the anti-PD-1 antibody has the same CDRs as nivolumab.

In another embodiment, the anti-PD-1 antibody (or an antigen-binding portion thereof) cross-competes with pembrolizumab. In some embodiments, the anti-PD-1 antibody binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also http://www.cancer.gov/drugdictionary?cdrid=695789 (last accessed: Dec. 14, 2014). Pembrolizumab has been approved by the FDA for the treatment of relapsed or refractory melanoma and advanced NSCLC.

In other embodiments, the anti-PD-1 antibody (or an antigen-binding portion thereof) cross-competes with MEDI0680. In some embodiments, the anti-PD-1 antibody binds to the same epitope as MEDI0680. In certain embodiments, the anti-PD-1 antibody has the same CDR regions as MEDI0680. In other embodiments, the anti-PD-1 antibody is MEDI0680 (formerly AMP-514), which is a monoclonal antibody against the PD-1 receptor MEDI0680 is described, for example, in U.S. Pat. No. 8,609,089B2 or in http://www.cancer.gov/drugdictionary?cdrid=756047 (last accessed Dec. 14, 2014).

In certain embodiments, an immune checkpoint inhibitor is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody (or an antigen-binding portion thereof) cross-competes with BGB-A317. In some embodiments, the anti-PD-1 antibody binds to the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

Anti-PD-1 antibodies usable in the disclosed methods also include isolated antibodies that bind specifically to human PD-1 and cross-compete for binding to human PD-1 with nivolumab (see, e.g., U.S. Pat. No. 8,008,449; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as nivolumab are monoclonal antibodies. For administration to human subjects, these cross-competing antibodies can be chimeric antibodies, or can be humanized or human antibodies. Such chimeric, humanized or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, or any combination thereof.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014). In yet other embodiments, the antibody comprises a light chain constant region which is a human kappa or lambda constant region. In other embodiments, the anti-PD-1 antibody or antigen-binding portion thereof is a monoclonal antibody or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0680 (formerly AMP-514), AMP-224, or BGB-A317.

In other embodiments, the anti-PD-1 antibody or antigen-binding portion thereof is a chimeric, humanized or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3 or IgG4 isotype may be used.

Anti-CD27 Antibodies

The combination therapy of the present invention also utilizes an anti-CD27 antibody or an antigen-binding fragment thereof. CD27 receptors are members of the tumor necrosis factor receptor superfamily required for generation and long-term maintenance of T cell immunity, and binds to CD70. CD27 is constitutively expressed on the majority of mature T cells, memory B cells, and a portion of natural killer cells.

Antibodies targeting CD27 can potentially be either agonists or antagonists of these CD27-CD70 pathway activities. In addition to the immune enhancing properties of agonist anti-CD27 monoclonal antibodies, CD27-targeting antibodies can also provide direct therapeutic effects against tumors with CD27 expression. CD27 has distinct properties, including a restricted distribution of expression, requirement for concomitant T cell receptor activation, comparable expression patterns in human and non-human primates in which toxicity studies have been conducted, and lack of observed toxicity in preclinical studies, that suggest agonist anti-CD27 monoclonal antibodies may have less acute toxicity than other agonist monoclonal antibodies targeting costimulatory molecules that have been studied in the clinic to date. In one embodiment, the anti-PD-1 antibody is varlilumab. Varlilumab (also known as "CDX-1127" and "1F5") is a human IgG1 antibody that is an agonist for human CD27. Varlilumab is described, for example, in U.S. Pat. No. 9,169,325; see also Vitale et al., *Clin Cancer Res.* 18(14): 3812-21 (2012); He et al., *Journal of Immunology* 191(8): 4174-83 (2013) and Thomas et al., *OncoImmunology* 3, e27255 (January 2014)). Varlilumab is currently in Phase 1 development. In one embodiment, the anti-CD27 antibody is anti-CD27 antibody or fragment thereof that binds to the same epitope as varlilumab. In certain embodiments, the anti-CD27 antibody is an antibody that has the same CDRs as varlilumab. Antibodies that bind to the same epitope are expected to have functional properties very similar to those of varlilumab by virtue of their binding to the same epitope region of CD27. These antibodies can be readily identified based on their ability to, for example, cross-compete with nivolumab in standard CD27 binding assays such as Biacore analysis, ELISA assays or flow cytometry.

In certain embodiments, the antibodies that cross-compete for binding to human CD27 with, or bind to the same epitope region of human CD27 as, varlilumab are monoclonal antibodies. For administration to human subjects, these cross-competing antibodies can be chimeric antibodies, or can be humanized or human antibodies. Such chimeric, humanized or human monoclonal antibodies can be prepared and isolated by methods well known in the art. Anti-CD27 antibodies usable in the methods of the disclosed invention also include antigen-binding portions of the above antibodies.

In other embodiments, the anti-CD27 antibody or antigen-binding portion thereof is a chimeric, humanized or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3 or IgG4 isotype may be used.

Cancer and Standard-of-Care Therapies

In some embodiments, the methods disclosed herein are used in place of standard of care therapies. In certain embodiments, a standard of care therapy is used in combination with any method disclosed herein. Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES®) that provide detailed up-to-date information on the standard-of-care treatments for a wide variety of cancers (see NCCN GUIDELINES®, 2014), available at: www.nccn.org/professionals/physician_gls/f_guidelines.asp, last accessed May 14, 2014).

Colorectal Cancer

In some embodiments, the combination therapy treats a cancer, which is colorectal cancer. In embodiments, the colorectal cancer is colon cancer. In other embodiments, the colorectal cancer is rectal cancer. In certain embodiments, the colorectal cancer has microsatellite instability (MSI). (See Pawlik et al., *Dis. Markers* 20(4-5): 199-206 (2004)) In other embodiments, the colorectal cancer has low microsatellite instability (MSI-L).

Colorectal cancer is the third most common type of cancer in both men and women in the U.S. (See http://www.cancer.gov/types/colorectal, last visited Dec. 9, 2015). Most colorectal cancers are adenocarcinomas. Colon cancer presents in five stages: Stage 0 (Carcinoma in Situ), Stage I, Stage II, Stage III and Stage IV. Six types of standard treatment are used for colon cancer: 1) surgery, including a local excision, resection of the colon with anastomosis, or resection of the colon with colostomy; 2) radiofrequency ablation; 3) cryosurgery; 4) chemotherapy; 5) radiation therapy; and 6) targeted therapies, including monoclonal antibodies and angiogenesis inhibitors. In some embodiments, the combination therapy of the invention treats a colon cancer along with a standard of care therapy.

Rectal cancer presents in five stages: Stage 0 (Carcinoma in Situ), Stage I, Stage II, Stage III and Stage IV. Six types of standard treatment are used for rectal cancer: 1) Surgery, including polypectomy, local excision, resection, radiofrequency ablation, cryosurgery, and pelvic exenteration; 2) radiation therapy; 3) chemotherapy; and 4) targeted therapy, including monoclonal antibody therapy. In some embodiments, the methods of the invention treat a rectal cancer along with a standard of care therapy.

Lung Cancer

In some embodiments, the combination therapy of the invention treats a cancer, which is lung cancer. In certain embodiments the cancer is NSCLC. In embodiments, the NSCLC has a squamous histology. In other embodiments, the NSCLC has a nonsquamous histology.

NSCLC is the leading cause of cancer death in the U.S. and worldwide, exceeding breast, colon and prostate cancer combined. In the U.S., an estimated 228,190 new cases of lung and bronchial will be diagnosed in the U.S., and some 159,480 deaths will occur because of the disease (Siegel et al. (2014) *CA Cancer J Clin* 64(1):9-29). The majority of patients (approximately 78%) are diagnosed with advanced/recurrent or metastatic disease. Metastases to the adrenal gland from lung cancer are a common occurrence, with about 33% of patients having such metastases. NSCLC therapies have incrementally improved OS, but benefit has reached a plateau (median OS for late stage patients is just 1 year). Progression after 1 L therapy occurred in nearly all of these subjects and the 5-year survival rate is only 3.6% in the refractory setting. From 2005 to 2009, the overall 5-year relative survival rate for lung cancer in the U.S. was 15.9% (NCCN GUIDELINES®, Version 3.2014—Non-Small Cell Lung Cancer, available at: www.nccn.org/professionals/physician_gls/pdf/nscl.pdf, last accessed May 14, 2014).

There are seven stages of NSCLC: Occult non-small cell lung cancer, Stage 0 (carcinoma in situ), Stage I, Stage II, Stage IIIA, Stage IIIB, and Stage IV. In some embodiments, the combination therapy of the invention treats a NSCLC along with a standard of care therapy.

In addition, the present methods can also be combined with surgery, radiation therapy (RT) and chemotherapy that are the three modalities commonly used to treat NSCLC patients. As a class, NSCLCs are relatively insensitive to chemotherapy and RT, compared to small cell carcinoma. In general, for patients with Stage I or II disease, surgical resection provides the best chance for cure, with chemotherapy increasingly being used both pre-operatively and post-operatively. RT can also be used as adjuvant therapy for patients with resectable NSCLC, the primary local treatment, or as palliative therapy for patients with incurable NSCLC.

In one embodiment, the subject suitable for the methods of the present invention is a patient with Stage IV disease. Patients with Stage IV disease have a good performance status (PS) benefit from chemotherapy. Many drugs, including platinum agents (e.g., cisplatin, carboplatin), taxanes agents (e.g., paclitaxel, albumin-bound paclitaxel, docetaxel), vinorelbine, vinblastine, etoposide, pemetrexed and gemcitabine are useful for Stage IV NSCLC. Combinations using many of these drugs produce 1-year survival rates of 30% to 40% and are superior to single agents. Specific targeted therapies have also been developed for the treatment of advanced lung cancer. For example, bevacizumab (AVASTIN®) is a monoclonal antibody that blocks vascular endothelial growth factor A (VEGF-A). Erlotinib (TARCEVA®) is a small-molecule TKI of epidermal growth factor receptor (EGFR). Crizotinib (XALKORI®) is a small-molecule TKI that targets ALK and MET, and is used to treat NSCLC in patients carrying the mutated ALK fusion gene. Cetuximab (ERBITUX®) is a monoclonal antibody that targets EGFR.

In some embodiments, the present methods are used to treat a subject who has squamous NSCLC. In certain embodiments, the present methods are used in combination with a standard of care therapy. There is a particular unmet need among patients who have squamous cell NSCLC (representing up to 25% of all NSCLC) as there are few treatment options after first line (1 L) therapy. Single-agent chemotherapy is standard of care following progression with platinum-based doublet chemotherapy (Pt-doublet), resulting in median OS of approximately 7 months. Docetaxel remains the benchmark treatment in this line of therapy although erlotinib can also be used with less frequency. Pemetrexed has also been shown to produce clinically equivalent efficacy outcomes but with significantly fewer side effects compared with docetaxel in the second line (2 L) treatment of patients with advanced NSCLC (Hanna et al., 2004 *J Clin Oncol* 22:1589-97). No therapy is currently approved for use in lung cancer beyond the third line (3 L) setting. Pemetrexed and bevacizumab are not approved in squamous NSCLC, and molecularly targeted therapies have limited application. The unmet need in advanced lung cancer has been compounded by the recent failure of Oncothyreon and Merck KgaA's STIMUVAX® to improve OS in a phase 3 trial, inability of ArQule's and Daiichi Sankyo's c-Met kinase inhibitor, tivantinib, to meet survival endpoints, failure of Eli Lilly's ALIMTA® in combination with Roche's AVASTIN® to improve OS in a late-stage study, and Amgen's and Takeda Pharmaceutical's failure to meet clinical endpoints with the small-molecule VEGF-R antagonist, motesanib, in late-stage trials.

Melanoma

In some embodiments, the combination therapy treats a cancer, which is melanoma. Melanoma is the most deadly form of skin cancer, and is the fifth most common cancer diagnosis in men and the seventh most common cancer diagnosis in women. (See http://www.cancer.gov/types/skin, last visited Dec. 9, 2015). Melanoma presents in seven stages: Stage 0 (Melanoma in situ), Stage I, Stage II, Stage III that can be removed by surgery, Stage III that cannot be removed by surgery, Stage IV, and Recurrent Melanoma. Five standard types of treatment are used: 1) surgery; 2) chemotherapy; 3) radiation therapy and 4) biologic therapy, including interferon, interleukin-2 (IL-2), tumor necrosis factor (TNF) therapy, and Ipilimumab, and 5) targeted therapy, including signal transduction inhibitor therapy (e.g., vemurafenib, dabrafenib, and trametinib), oncolytic virus therapy, monoclonal antibody therapy (including pembrolizumab and nivolumab), and angiogenesis inhibitors. In some embodiments, the combination therapy of the invention treats a melanoma along with a standard of care therapy Ovarian Cancer In certain embodiments, the combination therapy treats a cancer, which is ovarian, fallopian tube and primary peritoneal cancer ("ovarian cancer"). In certain embodiments, the cancer is ovarian epithelial cancer. In other embodiments, the cancer is ovarian germ cell tumor. In yet other embodiments, the cancer is an ovarian low malignant potential tumor. In embodiments, the ovarian cancer begins in the tissue that covers the ovaries, the peritoneum or the fallopian tube. (See http://www.cancer.gov/types/ovarian/patient/ovarian-epithelial-treatment-pdq, last visited Dec. 9, 2015)

There are four stages of ovarian cancer: Stage I, Stage II, Stage III, and Stage IV, which encompass early, advanced and recurrent or persistent ovarian cancer. There are four types of standard treatments that are used for patients with ovarian, fallopian tube and primary peritoneal cancer: 1) surgery, including hysterectomy, unilateral salpingo-oophorectomy, bilateral salpingo-oophorectomy, omentectomy, and lymph node biopsy; 2) radiation therapy; 3) chemotherapy; and 4) targeted therapy, including monoclonal antibody therapy and poly (ADP-ribose) polymerase inhibitors. Biologic therapies are also being tested for ovarian cancer. In some embodiments, the combination therapy of the invention treats an ovarian cancer along with a standard of care therapy.

There are four stages of ovarian germ cell tumors: Stage I, Stage II, Stage III and Stage IV. Four types of standard treatment are used: 1) surgery, including unilateral salpingo-oophorectomy, total hysterectomy, bilateral salpingo-oophorectomy, and tumor debulking; 2) observation; 3) chemotherapy and 4) radiation therapy. New treatment options being considered include high-dose chemotherapy with bone marrow transplant. In some embodiments, the combination therapy of the invention treats an ovarian germ cell tumor along with a standard of care therapy.

There are 3 stages of ovarian low malignant potential tumors: 1) early stage (Stage I and II), 2) late stage (Stage III and IB) and 3) recurrent. Two types of standard treatment are used: 1) surgery, including unilateral salpingo-oophorectomy, bilateral salpingo-oophorectomy, total hysterectomy, partial oophorectomy, and omentectomy and 2) chemotherapy. In some embodiments, the combination therapy of the invention treats an ovarian low malignant potential tumor along with a standard of care therapy.

Head and Neck Cancer

In some embodiments, the combination therapy treats a cancer, which is head and neck cancer. Head and neck cancers include cancers of the oral cavity, pharynx, larynx, paranasal sinuses and nasal cavity and salivary glands. Head and neck cancers usually begin in the squamous cells that line the moist, mucosal surfaces inside the head and neck (for example, inside the mouth, the nose, and the throat). These squamous cell cancers are often referred to as squamous cell carcinomas of the head and neck. Head and neck cancers can also begin in the salivary glands, but salivary gland cancers are relatively uncommon. (See http://www.cancer.gov/types/head-and-neck/head-neck-fact-sheet, last visited Dec. 9, 2015). The treatment plan for an individual patient depends on a number of factors, including the exact location of the tumor, the stage of the cancer, and the person's age and general health. Treatment for head and neck cancer can include surgery, radiation therapy, chemotherapy, targeted therapy, or a combination of treatments. In some embodiments, the combination therapy of the invention treats a head and neck cancer along with a standard of care therapy.

Pharmaceutical Compositions and Dosages

Therapeutic agents of the present invention can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In some embodiments, the carrier for a composition containing an antibody is suitable for intravenous, intramuscular, subcutaneous, parenteral, spinal or epidermal administration (e.g., by injection or infusion). A pharmaceutical composition of the invention can include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. In some embodiments, the anti-PD-1 antibody is administered at a weight-based dose. For administration of an anti-PD-1 antibody, the dosage can range from at least about 0.01 to at least about 20 mg/kg, from at least about 0.1 to at least about 10 mg/kg, from about 0.01 to about 5 mg/kg, from about 1 to about 5 mg/kg, from about 2 to about 5 mg/kg, from about 1 to about 3 mg/kg, from about 7.5 to about 12.5 mg/kg, or from about 0.1 to about 30 mg/kg of the subject's body weight. For example, dosages can be about 0.1, about 0.3, about 1, about 2, about 3, about 5 or about 10 mg/kg body weight. In certain embodiments, the dosage of the anti-PD-1 antibody is 3 mg/kg body weight.

In one embodiment, a dosage regimen for an anti-PD-1 antibody of the invention comprises about 0.3-1 mg/kg body weight, about 5 mg/kg body weight, 1-5 mg/kg body weight, or about 1-about 3 mg/kg body weight via intravenous administration, with the antibody being given every about 14-21 days in up to about 6-week or about 12-week cycles until complete response or confirmed progressive disease. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years.

In certain embodiments, the dose of an anti-PD-1 antibody is a fixed dose in a pharmaceutical composition. In other embodiments, the method of the present invention can be used with a flat dose (a dose given to a patient irrespective of the body weight of the patient). In some embodiments, the flat dose of the anti-PD-1 antibody is at least about 100 mg, 120 mg, 140 mg, 160 mg, 180 mg, 200 mg, 220 mg, 240 mg, 260 mg, 280 mg, 300 mg, 360 mg, 400 mg, 420 mg, 440 mg, 460 mg, 480 mg, 500 mg, 520 mg, 540 mg, 560 mg or 600 mg; at least about 100-300 mg, such as, at least about 200-300 mg, at least about 220-260 mg, at least about 230-250 mg or at least about 240 mg, such as at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg or at least about 300 mg. In some embodiments, the anti-PD-1 antibody is administered in a fixed dose with the anti-CD-27 antibody. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg anti-PD-1 antibody to mg anti-CD-27 antibody.

The dosing schedule is typically designed to achieve exposures that result in sustained receptor occupancy (RO) based on typical pharmacokinetic properties of an antibody. An exemplary treatment regime entails administration once per week, once about every 2 weeks, once about every 3 weeks, once about every 4 weeks, once about a month, once about every 3-6 months or longer. In certain embodiments, an anti-PD-1 antibody such as nivolumab is administered to the subject once about every 2 weeks. In other embodiments, the antibody is administered once about every 3 weeks. The anti-PD-1 antibody can be administered in at least two doses, each of the doses is at an amount of about 0.01 mg/kg to about 5 mg/kg, e.g., 3 mg/kg, at a dosing interval of every two weeks between the two doses. In some embodiments, the anti-PD-1 antibody is administered in at least three, four, five, six, or seven doses (i.e., multiple doses), each of the doses is at an amount of about 0.01 mg/kg to about 5 mg/kg, e.g., 3 mg/kg, at a dosing interval of every two weeks between two adjacently given doses. The dosage and scheduling can change during a course of treatment.

When used in combinations with other anti-cancer agents, the dosage of an anti-PD-1 antibody can be lowered compared to the monotherapy dose. Dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al. (2010) *J Clin Oncol* 28:3167-75). In some embodiments, 0.3 mg/kg dosing can allow for sufficient exposure to lead to maximal biologic activity.

In some embodiments, the anti-CD27 antibody is administered at a weight-based dose. For administration of an anti-CD27 antibody the dosage can range from about 0.01 to about 20 mg/kg, about 0.05 to about 20 mg/kg, about 0.1 to about 20 mg/kg, about 0.1 to about 15 mg/kg, about 0.1 to about 10 mg/kg, about 0.1 to about 5 mg/kg, and about 1 to about 10 mg/kg of the subject's body weight. For example, dosages can be about 0.05 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 20 mg/kg of the subject's body weight. In embodiments, the dosage of the anti-CD27 antibody is 0.1 mg/kg body weight. In other embodiments, the dosage of the anti-CD27 antibody is 1 mg/kg body weight. In further embodiments, the dosage of the anti-CD27 antibody is 10 mg/kg body weight. In certain embodiments, an anti-CD27 antibody is administered at a flat dose. In embodiments, the flat dose of the anti-CD27 is a dose (e.g., flat dose) of at least about 60-1500 mg, such as, at least about 100-1400 mg, at least about 100-1000 mg, at least about 200-1000 mg or at least about 200-500 mg, such as at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 600 mg, at least about 700 mg, at least about 800 mg, at least about 900 mg, at least about 1000 mg, at least about 1100 mg, at least about 1200 mg, at least about 1300 mg, at least about 1400 mg, or at least about 1500 mg.

An exemplary treatment regime entails administration once per week, once about every 2 weeks, once about every 3 weeks, once about every 4 weeks, once about a month, once about every 3-6 months or longer. In certain embodiments, the anti-CD27 antibody is administered once about every 2 weeks.

In some embodiments, a subtherapeutic dose of an anti-CD27 antibody is used in the methods herein. The subtherapeutic dosages of an anti-CD27 antibody used in the methods herein are higher than 0.001 mg/kg and lower than 10 mg/kg. In some embodiments, the subtherapeutic dose is about 0.001 mg/kg-about 10 mg/kg, about 0.01 mg/kg-about 10 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, at least about 1.0 mg/kg, at least about 2 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg or at least about 10 mg/kg body weight. In some embodiments, the subtherapeutic dose is about 10 mg/kg, about 5 mg/kg, about 2 mg/kg, about 1 mg/kg, about 0.1 mg/kg, or about 0.01 mg/kg body weight.

In certain embodiments, at least about 0.1 to about 10 mg/kg of the anti-CD27 antibody and at least about 3 mg/kg of the anti-PD1 antibody are administered to the subject once about every two weeks. In certain embodiments, at least about 0.1 mg/kg of the anti-CD27 antibody and at least about 3 mg/kg of the anti-PD1 antibody are administered to the subject once about every two weeks. In certain embodiments, at least about 1 mg/kg of the anti-CD27 antibody and at least about 3 mg/kg of the anti-PD1 antibody are administered to the subject once about every two weeks. In certain embodiments, at least about 10 mg/kg of the anti-CD27 antibody and at least about 3 mg/kg of the anti-PD1 antibody are administered to the subject once about every two weeks. In embodiments, the ant-CD27 antibody is varlilumab. In some embodiments, the an-PD-1 antibody is nivolumab.

In certain embodiments, the combination of an anti-PD-1 antibody and an anti-CD27 antibody is administered intravenously to the subject once about every 2 weeks for a total of eight weeks. In some embodiments, the eight week cycle is repeated 3 or 4 times. In embodiments, the subject is treated with a combination of an anti-PD-1 antibody and an anti-CD27 antibody every 2 weeks for a total of eight weeks and 3 eight-week cycles are performed. In embodiments, the subject is treated with a combination of an anti-PD-1 antibody and an anti-CD27 antibody every 2 weeks for a total of eight weeks and 4 eight-week cycles are performed. In embodiments, a subject is treated with the anti-PD1 antibody for 12 eight-week cycles.

Treatment is continued as long as clinical benefit is observed or until unacceptable toxicity or disease progression occurs. In certain embodiments, the anti-PD-1 antibody can be administered at the dosage that has been shown to produce the highest efficacy as monotherapy in clinical trials, e.g., about 3 mg/kg of nivolumab administered once about every three weeks (Topalian et al., 2012 *N Engl J Med* 366:2443-54; Topalian et al., 2012 *Curr Opin Immunol* 24:207-12), or at a significantly lower dose, i.e., at a subtherapeutic dose.

Dosage and frequency vary depending on the half-life of the antibody in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Kits

Also within the scope of the present invention are kits comprising an anti-PD-1 antibody and another anti-cancer agent for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) a dosage ranging from about 4 mg to about 500 mg of an anti-PD-1 antibody or antigen-binding portion thereof; and (b) a dosage ranging from about 0.4 mg to about 500 mg of an anti-CD27 antibody or antigen-binding portion thereof and (c) instructions for using the anti-PD-1 antibody and the anti-CD27 antibody in any of the combination therapy methods disclosed herein. In certain embodiments, the anti-PD-1 antibody, the anti-CD27 can be co-packaged in unit dosage form. In certain embodiments for treating human patients, the kit comprises an anti-human PD-1 antibody disclosed herein, e.g., nivolumab, pembrolizumab, MEDI0680 (formerly AMP-514), AMP-224, or BGB-A317. In other embodiments, the kit comprises an anti-human CD27 antibody disclosed herein, e.g., Varlilumab.

Throughout this application, various publications are referenced in parentheses by author name and date, or by patent No. or patent Publication No. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

The present invention is further illustrated by the following examples which should not be construed as further limiting. The contents of all references cited throughout this application are expressly incorporated herein by reference.

EXAMPLES

Example 1

A Phase I/II Dose Escalation and Cohort Expansion Study of the Safety, Tolerability and Efficacy of Anti-CD27 antibody (Varlilumab) Administered in Combination with Anti-PD-1 (Nivolumab) in Advanced Refractory Solid Tumors Objectives The primary objective of the Phase I study portion of this trial is to assess the safety and tolerability of varlilumab (0.1 to 10 mg/kg i.v. every 2 weeks) in combination with nivolumab (3 mg/kg i.v. every 2 weeks), and to identify dose limiting toxicities (DLTs) and the recommended Phase II dose of varlilumab for use in combination with nivolumab, in patients with advanced (metastatic and/or unresectable) solid tumors (non-small cell lung cancer (NSCLC), melanoma (MEL), colorectal cancer (CRC), ovarian cancer, and head and neck squamous cell carcinoma (SCCHN)).

The primary objective of the Phase II study portion of this trial is to assess the preliminary antitumor activity, as measured by objective response rate (ORR), of the combination of varlilumab and nivolumab in patients with specific advanced solid tumors (NSCLC, MEL, CRC, ovarian cancer, and SCCHN).

The secondary objectives of this study are: 1) to assess the pharmacokinetics (PK) of varlilumab when given in combination with nivolumab; 2) to determine the immunogenicity of varlilumab, when given in combination with nivolumab; and 3) to further assess the antitumor activity of combination treatment, as assessed by duration of response (DOR), time to response (TTR), progression-free survival (PFS), PFS at 24 weeks (PFS6), overall survival (OS) and landmark OS at two years (OS24) and three years (OS36) following the start of therapy with the combination of varlilumab and nivolumab.

The exploratory objectives of this study are: 1) to assess the pharmacodynamic effect in tumor tissue on tumor infiltrating lymphocyte (TIL) subsets from NSCLC, MEL, CRC, ovarian cancer and SCCHN in patients treated with varlilumab and nivolumab; 2) to assess the pharmacodynamic effects of varlilumab versus dose and/or exposure given in combination with nivolumab on biomarkers in peripheral blood, including T cell compartments, and serum proteins (cytokines and other immune modulators); 3) to explore potential associations between biomarker measures and anti-tumor activity; 4) to further characterize biomarker measures of immune functioning at multiple dose levels of varlilumab when given in combination with nivolumab; and 5) to examine any correlation of serum concentrations of varlilumab with toxicity and outcome.

Investigational Plan

Overall Design and Plan of the Study

This is a phase I/II, open label study of varlilumab and nivolumab combination therapy in patients with NSCLC, MEL, CRC, ovarian cancer or SCCHN. The tumor types selected for this study are intended to represent tumors with a range of responsiveness to nivolumab monotherapy. The Phase I part of the study will consist of a dose escalation assessment of the safety and tolerability of varlilumab (at doses ranging from 0.1 to 10 mg/kg), when administered with nivolumab (3 mg/kg). Patients with NSCLC, MEL, CRC, ovarian cancer or SCCHN will be enrolled during Phase I without restriction on the number of patients with each disease type allowed per cohort. The Phase II part of the study will include 5 disease-specific expansion cohorts, with sample size of either 18 or 35 evaluable patients, dependent on the cohort.

Emerging pharmacodynamic, pharmacokinetic, and clinical activity data will be evaluated by the sponsor and the Data Review Committee (DRC) throughout the course of dose-escalation, with the intent of identifying the recommended varlilumab dose level for further study in the Phase II study portion. If emerging data suggest that the recommended Phase II dose is reached before evaluation of all planned dose-levels in dose-escalation, the dose-escalation may be halted at the sponsor's discretion. In such cases, the DRC and Institutional Review Boards (IRB) will be notified. The varlilumab dose level selected for Phase II will not exceed the highest dose studied in dose-escalation.

As shown in FIG. 1 and Table 3, patient participation will include up to four study periods: Screening, Treatment, Clinical Follow-up, and Survival Follow-up. The Treatment Period may last for up to approximately two years, and will consist of up to 12 eight-week treatment cycles. Nivolumab may continue for up to a total of 12 treatment cycles, and varlilumab may continue for up to a total of 3 treatment cycles. After completion of the 3rd treatment cycle, upon consultation with and agreement by the Celldex Medical Monitor, patients who show evidence of an emerging response may receive one additional cycle of varlilumab.

In each eight-week cycle, study treatment(s) will be given once every two weeks for a total of four doses of each study treatment. Disease assessment will be performed every 8 weeks, and tumor response will be determined by the investigator in accordance with Response Evaluation Criteria for Solid Tumors (RECIST) 1.1. Patients who experience confirmed progression or clinical deterioration suggesting that no further benefit from treatment is likely, should discontinue therapy. In this protocol, subjects initially meeting radiologic criteria for disease progression will be allowed to continue study therapy until a second confirmation of progression performed approximately 8 weeks later, as long as the following criteria are met: 1) the subject experiences investigator-assessed clinical benefit; and 2) the subject is tolerating the study treatment.

Post-treatment, patients will enter the Clinical Follow-up period, with visits at 30, 60 and 100 days after the last dose of study treatment to monitor for adverse events. Subsequently, patients will enter the Survival Follow-up period, in which survival status will be assessed via clinic visits or telephone contact every 3 months for up to 3 years following the first dose of study drug. For patients who discontinue treatment in the absence of progression, tumor response assessments should continue through Clinical and Survival Follow-up until documented progression or initiation of alternate anticancer therapy.

Patients will not be permitted to have concurrent anticancer therapy, immunotherapy, or other experimental therapies during study treatment. During the Clinical Follow-up and Survival Follow-up period, additional anticancer therapies should be avoided if clinically feasible. If additional anticancer therapies are needed; it must be discussed and agreed upon with the Celldex Medical Monitor prior to administration.

Dose Escalation

A 3+3+3 design will be used to assess the safety of escalating doses of varlilumab, given in combination with nivolumab (3 mg/kg), as shown in Table 1.

TABLE 1

Design used to assess the safety of escalating doses of varlilumab given in combination with nivolumab

| Dose Level | Total Patients (n)* | Varlilumab Dose Level (mg/kg) | Nivolumab Dose Level (mg/kg) |
|---|---|---|---|
| 1 | ~6-15 | 0.1 | 3 |
| 2 | ~6-15 | 1 | 3 |
| 3 | ~6-15 | 10 | 3 |
| Total | ~18-45 | | |

The Dose Limiting Toxicity (DLT) observation period for each patient will be for 6 weeks after the first dose of study treatment. For the purpose of making decisions on dose escalation from a safety perspective, patients will be considered evaluable for DLT if they experience DLT or receive 2 out of the 3 scheduled nivolumab and varlilumab doses through the 6 week observation period without DLT. Patients who discontinue study treatment or who have dosing delays of ≥3 weeks during the DLT evaluation period for reasons other than a DLT may be replaced within the same dose level to ensure an adequate number of patients for dose-escalation evaluation and for pharmacodynamic, pharmacokinetic, and clinical activity data.

Up to 6 patients will initially be accrued to each cohort. Dose escalation or cohort expansion will proceed according to the following rules:

If 3 evaluable patients complete the DLT evaluation period without DLT, dose escalation may proceed.

If 1 patient experiences a DLT, the cohort will be further monitored until 6 patients complete the DLT evaluation period.

If no further DLT occur (for a total of 1 DLT in 6 evaluable patients), dose escalation may proceed.

If an additional DLT occurs (for a total of 2 DLT in 6 evaluable patients), the cohort will be expanded to a total of 9 patients.

If no further DLT occur (for a total of 2 DLT in 9 evaluable patients), dose escalation may proceed.

If ≥2 of 3, ≥3 of 6, or ≥3 of 9 patients in any cohort experience a DLT, that cohort will have exceeded the maximum tolerated dose (MTD). Patients continuing to receive treatment at this (or a higher) dose level should receive a reduced dose (the highest tolerated dose level) for the remainder of treatment.

If an adverse event (AE) occurs which requires adjudication as a potential DLT, and there is already a) a declared DLT or b) a previously occurring AE that has not been completely evaluated as a potential DLT, the cohort is at risk of exceeding the MTD. Therefore, new enrollment into the cohort will be held until the assessment of the potential DLT(s) is completed.

In particular, if there is a ≥30% frequency of grade ≥3 AEs attributed to study treatment, even if the AEs do not meet DLT criteria, the DRC will review the findings and new enrollment into the cohort may be held until further assessment by the DRC is completed.

The MTD will be defined as the dose level below that at which ≥2 of 3, ≥3 of 6, or ≥3 of 9 patients experience a DLT.

Although the dose-escalation rules above are based on evaluation of DLT through the first six weeks of treatment, continuous evaluation of toxicity will be performed by the DRC throughout the entire course of patient treatment. Specifically, each cohort will be monitored for delayed DLT (i.e., DLT occurring after 6 weeks), and in the event that delayed DLT result in an overall DLT rate for any cohort of more than 1 in 3 patients or at least 33% after treatment of the first 3 patients, further enrollment may be interrupted pending evaluation by the DRC. Similarly, if the overall AE data for a cohort suggest a significant safety concern (for example, if the rate of serious non-DLT events appears significantly increased beyond that observed with nivolumab monotherapy), the DRC may recommend against dose escalation or cohort expansion regardless of whether the DLT-based rules are met. Conversely, if the thresholds for cessation of dose-escalation are met (based on occurrence of DLT), but the DRC feel that further dose-escalation is justified, the DRC recommendation and plan will be communicated to the Food and Drug Agency (FDA) and IRBs prior to further dose-escalation.

In the event that a decision is made by the sponsor to reject a safety related recommendation by the DRC, the decision and rationale will be communicated to the FDA and site IRBs before enrolling additional patients.

Additional patients may be enrolled in any previously evaluated dose level cohort as necessary to reach 6 patients evaluable for pharmacodynamic, pharmacokinetic, and clinical activity data. If no MTD is reached through the completion of dose-escalation, all available clinical and laboratory data (including nature, time of onset and time to resolution of DLTs) will be reviewed through consultation between the investigators, the sponsor and the DRC to determine whether an alternative dose level/schedule should be examined. If agreed upon, the alternative level/schedule will be identified by a protocol amendment. After completion of dose-escalation, additional patients may be enrolled at dose level(s) of interest, for a total of up to 15 patients in any dose level cohort, to further explore pharmacodynamic/biomarker objectives.

Phase II

Patients enrolled in the Phase II study phase will receive the recommended Phase II dose of varlilumab in combination with nivolumab at 3 mg/kg. Five disease-restricted Phase II cohorts will gather additional safety, tolerability, preliminary efficacy and pharmacodynamic information regarding the combination of varlilumab and nivolumab, as shown in Table 2.

TABLE 2

Phase II cohorts

| Phase II Cohort | Tumor Type | Total Evaluable Patients |
|---|---|---|
| 1 | Non-small cell lung cancer (NSCLC) | 35 |
| 2 | Melanoma (MEL) | 35 |
| 3 | Colorectal cancer (CRC) | 18 |
| 4 | Ovarian | 18 |
| 5 | Head and Neck Squamous Cell Carcinoma (SCCHN) | 18 |
| Total | | 124 |

Continuous evaluation of toxicity and activity will be performed throughout enrollment in the Phase II cohorts. If the rate of DLTs exceeds more than 1 in 3 patients or at least 33% after treatment of the first 3 patients, the findings will be discussed and further enrollment may be interrupted. In addition, if there is a ≥30% frequency of grade ≥3 AEs attributed to study treatment, even if the AEs do not meet DLT criteria, the DRC will review the findings and new enrollment into the cohort may be held until further assessment by the DRC is complete. If a Phase II cohort is discontinued due to toxicity, a new cohort may be initiated at a previously tested lower dose level upon concurrence by the investigators, the sponsor and the DRC, and via protocol amendment. Similarly, upon consultation with the DRC, accrual to any cohort may be prematurely closed due to lack of observed activity.

The NSCLC and MEL cohorts, representing diseases in which nivolumab monotherapy has demonstrated activity, will be used to assess increased activity of the combination. In each of the NSCLC and MEL cohorts, 35 evaluable patients will be enrolled to allow for a more precise estimate of the objective response rate (ORR) in these tumors where activity for monotherapy has been established. The sample size of 35 patients allows for the 95% confidence interval (CI) about the estimated ORR to extend ≤35%.

The CRC, SCCHN, and ovarian cohorts will explore activity of the combination in tumors with unknown, or historically low, responses to nivolumab monotherapy. Eighteen evaluable patients will be enrolled per tumor cohort to allow for the 95% confidence interval (CI) about the estimated ORR to extend ≤48%.

Dose Limiting Toxicity

As noted above, DLTs that occur within 6 weeks of initiation of study drug will guide the conduct of dose escalation. For the purposes of patient management, DLTs will lead to permanent discontinuation of study treatments regardless of the cycle in which a DLT occurs.

All Adverse Events of Interest, including all potential DLT (regardless of time-frame for onset) and Grade ≥3 adverse events attributed to study treatment, will be reported to the Sponsor within 24 hours of the site's awareness of the occurrence of the event. For any patient who experiences a potential DLT, dosing should be held until completion of adjudication. Potential DLTs will be evaluated by the DRC as follows:

If any of the following occur, accrual will be held while the event is evaluated on an urgent basis by the DRC. The FDA and site IRBs will be notified of the event, results of adjudication, and determination regarding further enrollment:
Any grade 5 AE attributed to study treatment
Grade 4 colitis
Any perforation/colectomy
Grade 4 hepatic failure Any other grade 4 AE attributed to study treatment will be adjudicated to determine whether it represents a DLT with the exception of:
  Grade 4 lymphopenia
  Grade 4 neutropenia lasting ≤48 hours that is not associated with fever or other clinically significant symptoms
  Isolated, asymptomatic, reversible grade 4 laboratory abnormalities that are not considered clinically significant
  Grade 4 amylase or lipase abnormalities that are not associated with symptoms or clinical manifestations of pancreatitis. It is recommended to consult with the Celldex Medical Monitor for grade 4 amylase or lipase abnormalities.
Any grade 3 AE attributed to study treatment will be adjudicated to determine whether it represents a DLT with the exception of:
  Grade 3 AE that resolves to ≤grade 1 or to baseline within 3 weeks of its onset (may include events that resolve after medical treatment, including immunosuppressive therapy)
  Grade 3 lymphopenia
  Isolated, asymptomatic, reversible grade 3 laboratory abnormalities that are not considered clinically significant
  Grade 3 endocrinopathy that is adequately controlled by hormonal replacement
  Grade 3 adverse event of tumor flare (defined as local pain, irritation, or rash localized at sites of known or suspected tumor)
  Grade 3 infusion reaction that resolves within 6 hours to ≤grade 1 (may include events that resolve after medical treatment)
Any ≥grade 2 eye pain or reduction of visual acuity that does not improve to ≤grade 1 severity within 2 weeks of the initiation of topical therapy or requires systemic treatment will be adjudicated to determine whether it represents a DLT.

Dosing and Administration

In each eight-week cycle, varlilumab and nivolumab will be given once every two weeks for a total of four doses of each study treatment. In the absence of confirmed progression or clinical deterioration suggesting that no further benefit from treatment is likely, nivolumab may continue for up to a total of 12 treatment cycles (up to approximately 2 years), and varlilumab may continue for up to a total of 3 treatment cycles. After completion of the 3$^{rd}$ treatment cycle, upon consultation with and agreement by the Celldex Medical Monitor, patients who show evidence of an emerging response may receive one additional cycle of varlilumab for a total of 4 treatment cycles.

Varlilumab and nivolumab will be administered as separate infusions. Varlilumab and nivolumab should NOT be administered as a bolus injection or intravenous (IV) push. Separate infusion bags and filters must be used for each infusion, and each infusion should be followed by a saline flush to clear the line. For standardization purposes only, varlilumab should be the first infusion administered, followed by nivolumab. Varlilumab should be administered as a 90-minute infusion using a volumetric pump with a 0.2 micron pore size, low-protein binding polyethersulfone (PES) membrane in-line filter. After a break of at least 30 minutes, nivolumab will be given as a 60-minute infusion using a volumetric pump with a 0.2 to 1.2 micron pore size, low-protein binding polyethersulfone membrane in-line filter. All patients should be monitored for at least 1 hour following the last administration of study drug; patients who experience any treatment-related adverse events during the observation period should be further monitored as clinically appropriate.

The dose of varlilumab is based on cohort assignment (either 0.1, 1.0 or 10.0 mg/kg). Patients weighing >120 kg should receive a maximum of 1200 mg (240 ml) varlilumab. All patients will receive nivolumab at 3 mg/kg with rounding to the nearest milligram. The dose of study treatments will be calculated based on actual weight at enrollment (using weight obtained at either screen or Day 1) and may remain constant throughout the study unless greater than 10% change in weight is observed. Modifications to the administered dose of study drugs are not allowed, with one exception: patients who are receiving a dose level of varlilumab determined to exceed the MTD will be dropped down to the next lower dose level for any remaining treatment. Adjustments to the dosing schedule (treatment delays, infusion interruptions and infusion rate adjustments) will be allowed for treatment-related toxicity (non-DLT) in accordance with protocol defined criteria.

Prior to each study treatment administration, all toxicity related to prior treatment (including laboratory abnormalities, but excluding the specific exceptions noted in Study Treatment Dose Modifications) must resolve to ≤grade 1 and patients must be receiving ≤10 mg/day prednisone or equivalent for treatment of drug related toxicity. Treatment may be delayed for up to six weeks (from last dose) to allow sufficient time for recovery from treatment-related toxicities. If a delay greater than six weeks is required, the Investigator should confer with Celldex to determine the appropriateness of continued treatment.

Patients who experience any of the following will be ineligible for further treatment:
  Confirmed PD or clinical deterioration suggesting that no further benefit from treatment is likely;
  Therapy intolerance, defined by any of the following:
    DLT;
    Grade ≥3 drug-related uveitis, pneumonitis, bronchospasm, diarrhea, colitis, neurologic toxicity, or hypersensitivity reaction of any duration;
    Other grade ≥3 non-skin, drug-related toxicity lasting >7 days, with the following exceptions:
      Isolated, asymptomatic, reversible grade 3 laboratory abnormalities that are not considered clinically significant;
      Grade ≥3 endocrinopathy that is adequately controlled by hormonal replacement;
      Grade ≥3 adverse event of tumor flare (defined as local pain, irritation, or rash localized at sites of known or suspected tumor);
      Grade ≥3 infusion reaction that resolves within 6 hours to ≤grade 1; or
      Other Grade ≥3 toxicities of non-vital organs, after discussion with and concurrence from the Celldex Medical Monitor.
  For nivolumab: Completion of 12 cycles of treatment'
  For varlilumab: Completion of 3 cycles of treatment (or 4 cycles, upon consultation with and agreement by the Celldex Medical Monitor, for patients who show evidence of an emerging response); or
  Any other criteria for treatment discontinuation, as listed in Investigational Plan—Discontinuation of Study Treatment.

Selection of Study Population
Number of Patients
Up to approximately 190 patients will be treated.

Patient Eligibility

Inclusion Criteria: Patients must meet the following criteria prior to receiving study treatment to be eligible for participation in the study.

1. Read, understood, and (if applicable) provided written informed consent and, if applicable, Health Insurance Portability and Accountability Act (HIPAA) authorization after the nature of the study has been fully explained and must be willing to comply with all study requirements and procedures.
2. Advanced (unresectable and/or metastatic) histologically-diagnosed NSCLC; MEL, CRC, SCCHN, or ovarian cancer, meeting indication-specific eligibility criteria as specified in Tumor-Specific Inclusion/Exclusion Criteria.
3. No more than 3 prior anticancer regimens for advanced (recurrent, locally advanced or metastatic) disease (also see indication-specific eligibility criteria as specified in Tumor-Specific Inclusion/Exclusion Criteria).
4. Documented progressive disease, based on radiographic, clinical or pathologic assessment, at study entry.
5. All residual toxicity (excluding vitiligo, endocrinopathies on stable replacement therapy, alopecia, grade 2 fatigue, grade 2 neuropathy from taxanes or platinum and grade 2 hearing loss from platinum) related to prior anticancer therapies must resolve to grade 1 severity or less (or returned to baseline) prior to receipt of study treatment.
6. Measurable (target) disease by RECIST 1.1 criteria. Target lesions selected for tumor measurements should be those where additional (e.g., palliative) treatments are not indicated or anticipated.
7. Provision of consent for recent pre-treatment and on-treatment biopsies. Biopsy sites must be soft tissue tumor lesions that can be biopsied with acceptable clinical risk (as judged by the investigator); are large enough to allow for the collection of tumor tissue using a ≥18 gauge needle with an expected core sample length of 5 mm; and have not been irradiated prior to entry. Biopsy sites must be distinct from RECIST 1.1 target lesions, unless the biopsy is obtained more than 10 days prior to the Screening Disease Assessment. Pre-treatment tissue obtained by biopsy or resection performed according to standard of care may be utilized, provided tissue was obtained within 8 weeks of study entry, and subsequent to the last systemic anticancer therapy received. (Note: Initially, this criterion will apply to all patients enrolled into dose-escalation. If data obtained during the dose-escalation phase suggest that additional tissue collection will be of value, this criterion will additionally apply to the Phase II cohorts, until at least 10 patients in each cohort have successfully provided pre- and post-treatment tissue. Celldex will notify study centers when the requisite number of patients undergoing such biopsies has been reached, or when it is determined that further data is not needed, for each phase and cohort).
8. For patients who are not subject to the requirements of criterion 7: Tumor tissue (archived or recent) available for submission for retrospective biomarker analyses. If tumor tissue is not available, a subject may be enrolled in the study with prior permission of the Celldex Medical Monitor.
9. Male or female patient ≥18 years.
10. Life expectancy ≥12 weeks.
11. Eastern Cooperative Oncology Group (ECOG) Performance Status of 0 or 1.
12. Men enrolled in this trial must use effective contraception during the course of the trial and for at least 31 weeks after discontinuing study treatment, while women enrolled in this trial must use adequate birth control measures during the course of the trial and for at least 23 weeks after discontinuing study treatment. Effective contraception is defined as double barrier contraception (e.g., condom plus spermicide in combination with a female condom, diaphragm, cervical cap, contraceptive sponge or vaginal ring), intra-uterine device (IUD), implants, injectables, combined oral contraceptives, sexual abstinence (total abstinence from sexual intercourse as the preferred lifestyle of the patient; periodic abstinence is not acceptable), or sexual intercourse with only a vasectomized partner. Patients and/or partners who are surgically sterile or postmenopausal are exempt from this requirement.
13. Screening laboratory values must meet the following criteria:

| | | |
|---|---|---|
| a. | WBC | ≥2000/uL |
| b. | Neutrophils | ≥1500/uL |
| c. | Platelets | ≥100 × 10$^9$/L |
| d. | Hemoglobin | ≥9 g/dL |
| e. | Creatinine | ≤2 mg/dL |
| f. | AST | ≤2.5 × ULN without, and ≤5 × ULN with hepatic metastasis |
| g. | ALT | ≤2.5 × ULN without, and ≤5 × ULN with hepatic metastasis |
| h. | Total Bilirubin | ≤2 × ULN (except patients with Gilbert's syndrome or liver involvement, who must have a total bilirubin ≤3.0 mg/dL) |

Exclusion Criteria: Patients will be excluded from the study for any of the following reasons.

1. History of severe hypersensitivity reactions to other monoclonal antibodies.
2. Prior therapy with an anti-PD-1, anti-PD-L1, anti-PD-L2 antibody.
3. Receipt of anti-CTLA-4 or anti-CD27 antibody (or any other antibody targeting T cell check point or co-stimulation pathways) within 3 months prior to the planned start of study treatment.
4. Use of any monoclonal based therapies within 4 weeks, and all other immunotherapy (tumor vaccine, cytokine, or growth factor given to control the cancer) within 2 weeks prior to the first dose of study treatment.
5. Chemotherapy within 21 days or at least 5 half-lives (whichever is shorter) prior to the planned start of study treatment.
6. BRAF/MEK inhibitors within 2 weeks prior to the first dose of study treatment.
7. Systemic radiation therapy within 4 weeks, prior focal radiotherapy within 2 weeks, or radiopharmaceuticals (strontium, samarium) within 8 weeks prior to the first dose of study treatment.
8. Major surgery within 4 weeks prior to the first dose of study treatment. Surgery requiring local/epidural anesthesia must be completed at least 72 hours before study drug administration and subjects should be recovered.
9. Use of other investigational drugs within 2 weeks or 5 half-lives (whichever is longer) prior to study treatment administration.
10. Use of immunosuppressive medications within 4 weeks or systemic corticosteroids within 2 weeks prior to first dose of study treatment. Topical, inhaled or intranasal corticosteroids (with minimal systemic absorption) may be continued if the patient is on a stable dose. Non-absorbed intraarticular corticosteroid and replacement steroids (≤10 mg/day prednisone or equivalent) will be permitted.
11. Other prior malignancy, except for adequately treated basal or squamous cell skin cancer or in situ cancers; or any other cancer from which the patient has been disease-free for at least 3 years.
12. Active, untreated central nervous system metastases. Patients with brain metastases identified at Screening may be rescreened after the lesion(s) have been appropriately treated; patients with treated brain metastases should be neurologically stable for 4 weeks post-treatment and prior to study enrollment, and off corticosteroids for at least 2 weeks before administration of study drugs.
13. Active autoimmune disease or a documented history of autoimmune disease, or history of potential autoimmune syndrome that required systemic steroids or immunosuppressive medications, except for patients with vitiligo, endocrinopathies, type 1 diabetes, or patients with resolved childhood asthma/atopy or other syndromes which would not be expected to recur in the absence of an external trigger (e.g., drug-related serum sickness or post-streptococcal glomerulonephritis). Subjects with mild asthma who require intermittent use of bronchodilators (such as albuterol) who have not been hospitalized for asthma in the preceding 3 years will not be excluded from this study.
14. Active infection requiring systemic therapy, known HIV infection, or positive test for hepatitis B surface antigen or hepatitis C (antibody screen and if positive confirmed by RNA analysis). If positive results are not indicative of a true active or chronic infection, the patient can be enrolled after discussion with, and agreement by, the Celldex Medical Monitor.
15. Active diverticulitis.
16. Significant cardiovascular disease including unstable angina pectoris, uncontrolled hypertension or arrhythmia, congestive heart failure (NYHA Class III or IV) related to primary cardiac disease, ischemic or severe valvular heart disease, or a myocardial infarction within 6 months prior to the first dose of study treatment.
17. Underlying medical condition that, in the Principal Investigator's opinion, will make the administration of study treatment hazardous or obscure the interpretation of toxicity determination or adverse events.
18. Known alcohol or drug abuse.
19. Women who are pregnant or lactating. All female patients with reproductive potential must have a negative pregnancy test prior to starting treatment.

Measures to Minimize Bias

This is non-randomized open-label study. The analysis of tumor response and progression-free survival will be based on tumor response assessments performed by the investigator according to standardized, objective response criteria (RECIST 1.1). In addition, in the event of a positive study outcome, an additional assessment of tumor response and progression may be performed by an independent review committee (IRC) blinded to investigator assessments.

Withdrawals and Replacement of Patients

Every effort should be made within the bounds of safety and patient choice to have each patient complete the study. An explanation will be recorded for each patient taken off study treatment or discontinuing the study.

In the dose-escalation phase, patients who withdraw from the study before week 6 or receive less than 2 doses of each study treatment during the DLT evaluation period for reasons other than a DLT will be considered inevaluable for DLT assessment and will be replaced. In addition, patients who discontinue study treatment or who have dosing delays of ≥3 weeks during the DLT evaluation period for reasons other than DLT may be replaced, if necessary to ensure an adequate number of evaluable patients for dose-escalation decisions, pharmacodynamic, pharmacokinetic, and clinical activity data.

In the Phase II study portion, patients without an evaluable baseline tumor assessment or who discontinue study prior to the first disease assessment without symptomatic deterioration or death will be considered inevaluable and will be replaced.

Rationale for Permitting Continued Treatment in Cases of Suspected Progressive Disease Accumulating evidence indicates a minority of subjects treated with immunotherapy may derive clinical benefit despite initial evidence of progression per RECIST 1.1. Therefore, in order to ascertain whether true progression has occurred, or whether a treatment mediated inflammatory/immune mediated antitumor reaction (pseudoprogression) might have preceded a tumor response, patients with apparent progression may continue study treatment and complete the subsequent disease assessment on schedule, provided the following criteria are met:

Investigator-assessed clinical benefit. The assessment of clinical benefit should take into account whether the subject is clinically deteriorating and unlikely to receive further benefit from continued treatment.

Subject is tolerating study drug.

An optional tumor biopsy at time of progression can be considered when assessing whether to treat beyond progression. This may be particularly relevant to patients with melanoma in order to assess the current BRAF V600 mutational status at the time of progression. An optional tumor biopsy may also be utilized to investigate potential mechanisms of resistance to immunotherapeutic agents and the impact of treatment on relevant melanoma biomarkers. A portion of tumor tissue from a biopsy should be submitted to the central laboratory.

All decisions to continue treatment beyond initial progression must be discussed with the Celldex Medical Monitor and the patient, and the patient's consent for continued treatment after initial progression must be documented in the study records.

Subjects should discontinue study therapy upon further evidence of further progression, defined as an additional 10% or greater increase in tumor burden volume from time of initial progression (including all target lesions and new measurable lesions). For this assessment, new lesions are considered measurable at the time of initial progression if the longest diameter is at least 10 mm (except for pathological lymph nodes, which must have a short axis of at least 15 mm). Any new lesion considered non-measurable at the time of initial progression may become measurable and therefore included in the tumor burden measurement if the longest diameter increases to at least 10 mm (except for pathological lymph nodes, which must have an increase in short axis to at least 15 mm).

For statistical analyses that include the investigator-assessed progression date, subjects who continue treatment beyond initial investigator-assessed, RECIST 1.1- defined progression will be considered to have investigator-assessed progressive disease at the time of the initial progression event.

Discontinuation of Study Treatment

Patients who receive all allowed treatment cycles will be considered to have completed study treatment.

Reasons for permanent discontinuation of study treatment include:

Confirmed progressive disease, as assessed by the treating investigator in accordance with RECIST 1.1 criteria;

Symptomatic deterioration (clinical deterioration suggesting that no further benefit from treatment is likely);
  Note: This category is applicable to patients with a global deterioration of health status requiring discontinuation of treatment. However, per RECIST 1.1, symptomatic deterioration is not a descriptor of an objective response; it is a reason for stopping study therapy. Thus, every effort should be made to continue disease assessments per protocol until documented objective progression or initiation of alternate therapy.

Receipt of alternate anticancer treatments; or

Withdrawal request by the patient or the patient's legal representative.
  Note: Withdrawal of consent for continued study treatment should be differentiated from withdrawal of consent for study follow-up, and every effort should be made within the bounds of safety and patient choice to have each patient complete the study follow-up.

Adverse Event, including:
  DLT (See Study Treatment—Dose-Limiting Toxicity);
  Grade ≥3 drug-related uveitis, pneumonitis, bronchospasm, diarrhea, colitis, neurologic toxicity, or hypersensitivity reaction of any duration;
  Other grade ≥3 non-skin, drug-related toxicity lasting >7 days, with the following exceptions:
    Isolated, asymptomatic, reversible grade ≥3 laboratory abnormalities that are not considered clinically significant;
    Grade ≥3 endocrinopathy that is adequately controlled by hormonal replacement;
    Grade ≥3 adverse event of tumor flare (defined as local pain, irritation, or rash localized at sites of known or suspected tumor);
    Grade ≥3 infusion reaction that resolves within 6 hours to ≤grade 1; or
    Other Grade ≥3 toxicities of non-vital organs, after discussion with and concurrence from the Celldex Medical Monitor.

Physician Decision;

Non-compliance of the patient;

Pregnancy;

Death, otherwise not explainable by the above options; or

Patient lost to follow-up.

Patients who discontinue study treatment should be seen for an End of Treatment Visit. Patients who discontinue study treatment in the absence of progression will continue to have tumor assessments until documented progression or initiation of alternate anticancer therapies (see Table 3).

Discontinuation from the Study

Reasons for patient removal from the study include:
  Request of the patient or the patient's legal representative (withdrawal of consent for the study follow-up); or
  Patient lost to follow-up. A patient should be considered lost to follow up only after multiple efforts have been made to contact the patient to assess his/her health status after failure of the patient to attend scheduled visits. If after 2 documented phone calls the investigative site is still unable to contact the patient, a certified letter should be sent to his/her home for immediate response. If there is still no response, the patient is to be considered lost to follow up. A record of the patient being lost to follow up should be noted in the source documents along with the phone contacts and the returned certified mail (if sent back).

Completion of the Study

Patient participation will encompass a Screening Period of up to 28 days, a Treatment Period of up to approximately 2 years, a Clinical Follow-up Period of up to 100 days, and a Survival Follow-up Period lasting for up to 3 years from initiation of study treatment, or until death, discontinuation from study follow-up, or termination/completion of study.

It is anticipated that the enrollment period will be approximately 2.5 years. The study will be declared complete when sufficient data is obtained to conclude the study; this is estimated at approximately 5.5 years from the time of the first visit of the first patient to the required survival follow-up of the last patient enrolled.

Premature termination of this study may occur because of a regulatory authority decision, drug safety issues, or at the discretion of Celldex. In addition, Celldex and BMS retain the right to discontinue development of varlilumab and nivolumab, respectively, at any time.

Study Treatment

Varlilumab Preparation

The varlilumab dose to be administered will be diluted to a final volume of 90 ml for infusion, according to the instructions provided by Celldex in the pharmacy manual. No dilution is necessary in cases where the drug volume is greater than 90 ml.

Nivolumab Preparation

Nivolumab injection can be infused undiluted (10 mg/mL) or diluted with 0.9% Sodium Chloride Injection, USP or 5% Dextrose Injection, USP to protein concentrations as low as 1 mg/mL. Instructions for dilution and infusion of nivolumab injection will be provided in the pharmacy manual. Care must be taken to assure sterility of the prepared solution as the product does not contain any antimicrobial preservative or bacteriostatic agent. No incompatibilities between nivolumab and polyvinyl chloride (PVC), non-PVC/non-DEHP (di(2-ethylhexyl)phthalate) IV components, or glass bottles have been observed.

Administration of Study Treatments

The Treatment Period may last for up to approximately two years. In the absence of confirmed progression or clinical deterioration suggesting that no further benefit from treatment is likely, nivolumab may continue for up to a total of 12 treatment cycles (up to ~2 years), and varlilumab may continue for up to a total of 3 treatment cycles. After completion of the 3rd treatment cycle, upon consultation and with agreement by the Celldex Medical Monitor, patients who show evidence of an emerging response may receive one additional cycle of varlilumab for a total of 4 treatment cycles. In each eight-week cycle, varlilumab and nivolumab will be given once every two weeks for a total of four doses of each study treatment.

Varlilumab and nivolumab will be administered as separate infusions. Varlilumab and nivolumab should NOT be administered as a bolus injection or IV push. Separate infusion bags and filters must be used for each infusion, and each infusion should be followed by a saline flush to clear the line. For standardization purposes only, varlilumab should be the first infusion administered, followed by nivolumab. Varlilumab should be administered as a 90-minute infusion using a volumetric pump with a 0.2 micron pore size, low-protein binding polyethersulfone (PES) membrane in-line filter. After a break of at least 30 minutes, nivolumab will be given as a 60-minute infusion using a volumetric pump with a 0.2 to 1.2 micron pore size, low-protein binding polyethersulfone membrane in-line filter. All patients should be monitored for at least 1 hour following the last administration of study drug; patients who experience any treatment-related adverse events during the observation period should be further monitored as clinically appropriate.

The dose of varlilumab is based on cohort assignment (either 0.1, 1.0 or 10.0 mg/kg). Patients weighing >120 kg should receive a maximum of 1200 mg (240 ml) varlilumab. All patients will receive nivolumab at 3 mg/kg, with rounding to the nearest milligram. The dose of study treatments will be calculated based on actual weight at enrollment (using weight obtained at either screen or Day 1) and may remain constant throughout the study unless greater than 10% change in weight is observed.

Dose Modifications

Modifications to the administered dose of study drugs are not allowed, with one exception: patients who are receiving a dose level of varlilumab determined to exceed the MTD will be dropped down to the next lower dose level for any remaining treatment.

Adjustments to the dosing schedule (treatment delays, infusion interruptions and infusion rate adjustments) will be allowed for treatment-related toxicity (non-DLT) as follows:
  Prior to each study treatment administration, patients must be receiving ≤10 mg/day prednisone or equivalent for treatment of drug related toxicity, and all toxicity related to prior treatment (including laboratory abnormalities) must resolve to ≤grade 1 with the following exceptions:
    Subjects may resume treatment in the presence of grade 2 fatigue
    Subjects who have not experienced a grade 3 drug-related skin AE may resume treatment in the presence of grade 2 skin toxicity
    Subjects with baseline grade 1 AST/ALT or total bilirubin who require dose delays for reasons other than a 2-grade shift in AST/ALT or total bilirubin may resume treatment in the presence of grade 2 AST/ALT or total bilirubin
    Grade 2 drug-related pulmonary toxicity, diarrhea, or colitis, must have resolved to baseline before treatment is resumed
    Patients with drug-related endocrinopathies adequately controlled with only physiologic hormone replacement may resume treatment
  Treatment may be delayed for up to six weeks (from last dose) to allow sufficient time for recovery from treatment-related toxicities. If a delay greater than six weeks is required, the Investigator should confer with Celldex to determine the appropriateness of continued treatment. A minimum of 12 days must elapse between each repeated study drug administration.

Dose-Limiting Toxicity

DLTs that occur within 6 weeks of initiation of study drug will guide the conduct of dose escalation. For the purposes of patient management, DLTs will lead to permanent discontinuation of study treatments, regardless of the cycle in which a DLT occurs.

All Adverse Events of Interest, including all potential DLT (regardless of time-frame for onset) and Grade ≥3 adverse events attributed to study treatment, will be reported to the Sponsor within 24 hours of the site's awareness of the occurrence of the event. For any patient who experiences a potential DLT, dosing should be held until completion of adjudication. Potential DLTs will be evaluated by the DRC as follows:
  If any of the following occur, accrual will be held while the event is evaluated on an urgent basis by the DRC. The FDA and site IRBs will be notified of the event, results of adjudication, and determination regarding further enrollment:
    Any grade 5 AE attributed to study treatment;
    Grade 4 colitis;
    Any perforation/colectomy; or
    Grade 4 hepatic failure.
  Any other grade 4 AE attributed to study treatment will be adjudicated to determine whether it represents a DLT with the exception of:
    Grade 4 lymphopenia;
    Grade 4 neutropenia lasting ≤48 hours that is not associated with fever or other clinically significant symptoms;
    Isolated, asymptomatic, reversible grade 4 laboratory abnormalities that are not considered clinically significant; or
    Grade 4 amylase or lipase abnormalities that are not associated with symptoms or clinical manifestations of pancreatitis. It is recommended to consult with the Celldex Medical Monitor for grade 4 amylase or lipase abnormalities.
  Any grade 3 AE attributed to study treatment will be adjudicated to determine whether it represents a DLT with the exception of:
    Grade 3 AE that resolves to ≤grade 1 or to baseline within 3 weeks of its onset (may include events that resolve after medical treatment, including immunosuppressive therapy);
    Grade 3 lymphopenia;
    Isolated, asymptomatic, reversible grade 3 laboratory abnormalities that are not considered clinically significant;
    Grade 3 endocrinopathy that is adequately controlled by hormonal replacement;
    Grade 3 adverse event of tumor flare (defined as local pain, irritation, or rash localized at sites of known or suspected tumor); or
    Grade 3 infusion reaction that resolves within 6 hours to ≤grade 1 (may include events that resolve after medical treatment).
  Any ≥grade 2 eye pain or reduction of visual acuity that does not improve to ≤grade 1 severity within 2 weeks of the initiation of topical therapy or requires systemic treatment will be adjudicated to determine whether it represents a DLT.

Management of Toxicity

Varlilumab monotherapy appears to have less acute toxicity then other agonist antibodies, perhaps due to the distinct properties of CD27, including a restricted distribution of expression, and requirement for concomitant T cell receptor activation. Nonetheless, the clinical experience to date is relatively limited and investigators should be cognizant of the potential for unpredicted acute and chronic toxicity associated with varlilumab. In addition, there is potential for increased frequency and/or severity of toxicity in combining varlilumab and nivolumab and patients must be closely monitored for toxicity. Toxicity should be aggressively worked-up and appropriately managed per the guidelines provided in this protocol, the Nivolumab Investigator's Brochure and the Varlilumab Investigator's Brochure.

Patients receiving varlilumab and/or nivolumab should be monitored for signs and symptoms of enterocolitis, dermatitis, hepatotoxicity, neuropathy, pulmonary toxicity and endocrinopathy. Patients should be advised to immediately report symptoms such as unexplained abdominal pain, diarrhea, nausea or vomiting, severe rash or vision changes. Patients with unexplained symptoms such as fatigue, myalgias, impotence, mental status changes, or constipation should be investigated for the presence of thyroid, pituitary or adrenal endocrinopathies.

Laboratory tests must be performed as outline in Table 3 and results reviewed prior to dosing as outlined in footnote 10. Visual complaints should be investigated by an ophthalmologist. Patients should be observed for at least one hour after the last study drug administration to monitor for infusion reaction/cytokine release syndrome/hypersensitivity reaction. Acetaminophen may be used to manage drug-related adverse events such as fever, myalgias or arthralgias and anti-histamines may be used to manage drug-related adverse events such pruritus.

Infusion Reactions

Nivolumab and varlilumab contains only human immunoglobulin protein sequences and are unlikely to be immunogenic. Infusion or hypersensitivity reactions are expected to be infrequent events. However, if such a reaction were to occur, it might manifest with fever, chills, rigors, headache, rash, pruritus, arthralgias, hypo- or hypertension, bronchospasm, or other symptoms. All grade 3 or 4 infusion reactions should be reported within 24 hours to the Celldex Medical Monitor and reported as a serious adverse event (SAE) if criteria are met. Infusion reactions should be graded according to National Cancer Institute of the United States (NCI) Common Toxicity Criteria for Adverse Events (CTCAE) (version 4.0) guidelines.

Treatment recommendations are provided below and may be modified based on local treatment standards and guidelines as appropriate:

For grade 1 symptoms: (Mild reaction; infusion interruption not indicated; intervention not indicated)
Remain at bedside and monitor subject until recovery from symptoms. The following prophylactic premedications are recommended for future infusions: diphenhydramine 50 mg (or equivalent) and/or paracetamol 325 to 1000 mg (acetaminophen) at least 30 minutes before additional nivolumab administrations.

For grade 2 symptoms: (Moderate reaction requires therapy or infusion interruption but responds promptly to symptomatic treatment [e.g., antihistamines, non-steroidal anti-inflammatory drugs, narcotics, corticosteroids, bronchodilators, IV fluids]; prophylactic medications indicated for ≤24 hours)
Stop the nivolumab or varlilumab infusion, begin an IV infusion of normal saline, and treat the subject with diphenhydramine 50 mg IV (or equivalent) and/or paracetamol 325 to 1000 mg (acetaminophen); remain at bedside and monitor subject until resolution of symptoms. Corticosteroid or bronchodilator therapy may also be administered as appropriate. If the infusion is interrupted, then restart the infusion at 50% of the original infusion rate when symptoms resolve; if no further complications ensue after 30 minutes, the rate may be increased to 100% of the original infusion rate. Monitor subject closely. If symptoms recur then no further nivolumab or varlilumab will be administered at that visit. Administer diphenhydramine 50 mg IV, and remain at bedside and monitor the subject until resolution of symptoms. The amount of study drug infused must be recorded on the electronic case report form (eCRF). The following prophylactic premedications are recommended for future infusions: diphenhydramine 50 mg (or equivalent) and/or paracetamol 325 to 1000 mg (acetaminophen) should be administered at least 30 minutes before additional nivolumab or varlilumab administrations. If necessary, corticosteroids (recommended dose: up to 25 mg of IV hydrocortisone or equivalent) may be used.

For grade 3 or grade 4 symptoms: (Severe reaction, grade 3: prolonged [i.e., not rapidly responsive to symptomatic medication and/or brief interruption of infusion]; recurrence of symptoms following initial improvement; hospitalization indicated for other clinical sequelae [e.g., renal impairment, pulmonary infiltrates]. Grade 4: life-threatening; pressor or ventilatory support indicated.)
Immediately discontinue infusion of nivolumab or varlilumab. Begin an IV infusion of normal saline, and treat the subject as follows. Recommend bronchodilators, epinephrine 0.2 to 1 mg of a 1:1,000 solution for subcutaneous administration or 0.1 to 0.25 mg of a 1:10,000 solution injected slowly for IV administration, and/or diphenhydramine 50 mg IV with methylprednisolone 100 mg IV (or equivalent), as needed. Subject should be monitored until the investigator is comfortable that the symptoms will not recur. Nivolumab or varlilumab will be permanently discontinued. Investigators should follow their institutional guidelines for the treatment of anaphylaxis. Remain at bedside and monitor subject until recovery from symptoms. In the case of late-occurring hypersensitivity symptoms (e.g., appearance of a localized or generalized pruritus within 1 week after treatment), symptomatic treatment may be given (e.g., oral antihistamine, or corticosteroids).

Concomitant Therapy

Refer to the study entry criteria for the required "washout" period for specific therapies, relative to start of study treatment. Patients may continue to use any ongoing medications not prohibited by the inclusion/exclusion criteria. However, efforts should be made to maintain stable doses of concomitant medications during the course of study treatment.

While on study, when clinically appropriate, patients should strictly follow the study-prescribed treatment regimen in accordance with the following guidance:
Concurrent administration of any anticancer therapies and/or other investigational agents are prohibited throughout the treatment period.
Following treatment but prior to documented progression of disease, additional anticancer therapies should be avoided if clinically feasible. If additional anticancer therapies are needed; it should be discussed and agreed upon with the Celldex Medical Monitor prior to administration.
Following progression of disease, patients may receive any appropriate alternate therapies.

During study treatment, patients may receive supportive care to include bisphosphonates, hematologic and anti-infectious support and pain management. Thoracocentesis or paracentesis may be administered, if needed for comfort. If surgical intervention or localized radiation become indicated (either for palliation or down-staging of previously non-resectable tumor), these interventions are permitted, but should be avoided if clinically feasible until after the second response assessment, following consultation with the Celldex Medical Monitor. A tumor response assessment should be conducted prior to any intervention, in order to document progression and/or confirm an objective response. Patients who undergo surgical resection or radiation in the absence of progression may continue to receive study treatment until remaining lesions meet criteria for progression of disease.

Immunosuppressive agents are prohibited during the study, with the following exceptions:

Immunosuppressive agents and the use of systemic corticosteroids are permitted in the context of treating adverse events. Subjects receiving corticosteroids for treatment of drug-related adverse events must be at ≤10 mg/day prednisone or equivalent prior to re-initiation of study therapy Subjects are permitted the use of topical, ocular, intra-articular, intranasal, and inhalational corticosteroids (with minimal systemic absorption).

Any vaccination containing live, attenuated, or inactivated virus may be permitted if clinically indicated. However, this must be discussed with the Celldex Medical Monitor prior to administration and may require a study drug washout period prior to and after administration of the vaccine. Inactivated influenza vaccination is permitted on study without restriction.

Pre-medication as prophylaxis for infusion reaction should only be initiated if clinically indicated.

The effect of varlilumab and nivolumab on the absorption, metabolism, or excretion of other drugs has not been studied. As varlilumab and nivolumab are human monoclonal antibodies, inhibition or induction of cytochrome P450 (CYP) enzymes or other typical drug metabolizing enzymes is unexpected, and thus, interaction with other medications metabolized through these pathways is unlikely.

All concomitant medication will be documented in the eCRF if taken within 28 days prior to initiation of study treatment, until 100 days after last dose of study treatment. In addition, all anticancer surgeries or treatments, and response to those treatments, should be recorded throughout the duration of study follow-up.

Study Procedures

Study Enrollment

Patients who are screened and do not meet all entry criteria will not be entered in the clinical database. Once assigned, numbers for any screening failures, non-treated, non-evaluable, or discontinued patients will not be re-used.

Enrollment should occur in accordance with instructions provided by Celldex, only after confirming all inclusion criteria and none of the exclusion criteria have been met.

Treatment Phase

Specific procedures to be performed at each visit during the treatment phase are illustrated in the Study Assessment Schedule Table 3.

In each eight-week cycle, varlilumab and nivolumab will be given once every two weeks for a total of four doses of each study treatment. Disease assessment will be performed between each cycle, and tumor response will be determined by the investigator in accordance with RECIST 1.1. In the absence of confirmed progression or clinical deterioration suggesting that no further benefit from treatment is likely, nivolumab may continue for up to a total of 12 treatment cycles, and varlilumab may continue for up to a total of 3 treatment cycles. After completion of the 3rd treatment cycle, upon consultation with and agreement by the Celldex Medical Monitor, patients who show evidence of an emerging response may receive one additional cycle of varlilumab for a total of 4 treatment cycles.

Patients will enter the Clinical Follow-up Period after discontinuation of both study treatments.

The End of Treatment visit should be performed within 28 days after last study drug dosing and prior to initiation of alternate therapies. This visit may be combined with the 30-day post-treatment follow-up visit, if the windows overlap, with required assessments completed once for the combined visit.

Clinical Follow-Up

The post-treatment Clinical Follow-up period will include visits at 30, 60 and 100 days after the last dose of study treatment to monitor for adverse events.

Patients who discontinue treatment in the absence of progression will continue to have tumor assessments until documented progression or initiation of alternate anticancer therapies, in accordance with Table 3.

Survival Follow-Up

Subsequent to the Clinical Follow-up Period, patients will enter the Survival Follow-up period, in which survival status will be assessed via clinic visits or telephone contact every 3 months for up to 3 years following the first dose of study drug.

Patients who discontinue treatment in the absence of progression will continue to have tumor assessments until documented progression or initiation of alternate anticancer therapies, in accordance with Table 3.

Methods of Assessment

Antitumor Activity: Antitumor activity will be assessed via ORR, DOR, TTR, PFS, PFS6, OS, OS24 and OS36. Primary analyses will utilize investigator assessments in accordance with RECIST 1.1 criteria. Supplementary analyses of tumor response and progression may also be performed using "irRECIST" criteria (in which new lesions do not constitute progression, but contribute to the calculated sum of diameter of all measurable disease) and/or performed by a central IRC blinded to investigator assessments.

Immunogenicity: Patients will be monitored for the development of human anti-varlilumab and anti-nivolumab antibody response assessments. In addition, serum samples designated for Pharmacokinetics (PK) or biomarker assessments may also be used for immunogenicity analysis if required (e.g., insufficient volume for complete immunogenicity assessment or to follow up on suspected immunogenicity related AE).

Pharmacokinetic Evaluations: Concentrations of varlilumab and nivolumab will be determined using Good Laboratory Practices (GLP) compliant Enzyme-Linked Immunosorbent Assay (ELISA) and liquid chromatography-mass spectrometry/mass spectrometry (LC-MS/MS) methods. In addition, selected samples may be analyzed by an exploratory method for technology exploration purposes; exploratory data will not be reported.

Pharmacodynamics: In this study we plan to analyze cellular and serum samples collected at baseline, during and after treatment from subjects enrolled on the trial to identify potential biomarkers with prognostic and predictive value for outcomes (response, progression-free survival and overall survival, toxicity). Preliminary results from this study will inform the dose effect of varlilumab and may help in selection of the appropriate dose for the phase II efficacy study.

Soluble Biomarkers: Soluble factors, such as cytokines, chemokines and soluble receptors will be quantified in serum. Analyses may include, but not necessarily be limited to sCD27, sCD40 L, IL-6 and CXCL-10. Collected serum samples may also be used for the assessment of humoral immune responses to explore if treatment augments and/or induces antitumor or other antibodies responses. In general, these soluble markers will be assessed by multiplex assays and enzyme-linked immunosorbent assay (ELISA). In addition, selected samples may be analyzed by exploratory methods for technology exploration purposes; exploratory data will not be reported.

Immunophenotyping: The proportion of specific lymphocyte subsets in peripheral blood mononuclear cell (PBMC) preparations will be quantified by flow cytometry. Analyses may include, but not necessarily be limited to, the proportion of T, B, MDCS and NK cells, the proportion of memory, effector and regulatory T cell subsets, and expression levels of CD27, PD-1, other B7 family members, ICOS, Ki67, and T cell activation markers such as HLA-DR.

Ex Vivo Functional Assays: To explore the effects of treatment on T cell activation and function, peripheral blood mononuclear cells (PBMCs) will be isolated and tested fresh or cryopreserved. Assays of the functional status of effector T cells may be performed, including but not limited to, assays for cytokine production and expression of costimulatory/coinhibitory markers. These methods may include re-stimulation of peripheral blood T cells using relevant tumor or recall antigens or mitogens followed by measurement of effector cytokines such as IFN-g using ELISPOT.

Peripheral Blood Gene Expression: The expression composition and pattern of genes will be quantified by molecular methods such as microarray and/or quantitative reverse transcription polymerase chain reaction (RT-PCR) analysis in whole blood samples collected in Paxgene tubes. Analysis may include, but not necessarily be limited to, genes associated with immune-related pathways, such as T cell activation, antigen processing and presentation, and FcRgamma polymorphisms.

Tumor Biopsies: Analysis of the tumor microenvironment may be very informative when correlated to the proposed mechanisms of action and to clinical outcome. Analysis such as immunohistochemistry (IHC) can be performed on fixed tissues from archived samples as well as those collect on study. Fresh biopsy specimens may be used for functional analysis such as cytokine expression. Biomarkers of particular interest include the ligands for varlilumab and nivolumab, CD70 and PD-L1, respectively. In addition, characterization of the immune infiltrate using markers for T cell subsets, and other immune cells will be evaluated.

Criteria for Evaluation

Safety

Safety will be assessed by the incidence of adverse events (graded according to National Cancer Institute (NCI) Common Toxicity Criteria for Adverse Events (CTCAE) version 4.0), electrocardiograms (ECG), vital signs, physical exams, laboratory test results and immunogenicity assessment. Given the expected mechanism of action of the study drugs, particular attention will be given to adverse events that may be secondary to activation of the immune system and have been observed with other immune-stimulatory antibodies; such events include diarrhea/colitis, rash, endocrinopathies, and hepatitis.

Pharmacokinetics

The nivolumab and varlilumab pharmacokinetic concentrations will be measured to derive the trough ($C_{min}$) and end of infusion concentration at specified visits.

Biomarker Measures

As described in Table 3, pre-treatment, on-treatment, and possibly post-treatment tumor biopsies, as well as matched peripheral blood samples, will be collected for a subset of patients to explore the relationship between the presence of lymphocyte subsets and the expression of selected tumor markers, using studies including but not limited to:

Characterization of Tumor Infiltrating Lymphocytes (TILs), including lymphocyte subpopulations, CD27 expression, and activation markers Expression of tumor markers including CD70, PD-L1 and HLA Class I Studies conducted on peripheral blood specimens may include but are not limited to:

T cell functional assessment

Immunophenotyping of NK cell, B cell, MDSC and T cell subsets

Immune modulation analysis of soluble factors including cytokines

HLA and FcRgamma genotyping

Immunogenicity

Serum samples will be obtained for assessment of human anti-varlilumab and anti-nivolumab antibody response, as described in the Schedule of Assessments.

Activity Evaluations

Antitumor activity will be assessed via ORR, DOR, TTR, PFS, PFS6, OS, OS24 and OS36.

Statistical Analysis

Safety: Safety and tolerability will be assessed by incidence, severity, and changes from baseline of all relevant parameters including AEs, DLT, ECGs, laboratory values, and vital signs. Safety data analysis will be conducted on all patients receiving at least one dose of either study drug. AEs will be coded using the latest available version of the Medical Dictionary for Regulatory Activities (MedDRA). Treatment-emergent AEs are defined as AEs that start on or after the first day study drug is administered. The number and percentage of patients experiencing one or more treatment-emergent AEs will be summarized by treatment cohort, relationship to study drug, and severity. A patient reporting multiple cases of the same AE will be counted once within each system organ class and similarly counted once within each preferred term. Unless specified otherwise, the denominator for these calculations will be based on the number of patients in each treatment cohort who receive at least one (1) dose of study drug, irrespective of the total number of doses administered. Additional summaries may also be provided for SAEs and events resulting in the permanent discontinuation of therapy. All AEs will be included in individual patient data listings. Laboratory parameters will be summarized using descriptive statistics, by post-dosing shifts relative to baseline, and in data listings. Vital sign results (systolic and diastolic blood pressure, pulse, respiration, and temperature) will be summarized by changes from baseline values using descriptive statistics. ECG results will be evaluated by the investigator and abnormalities, if present, will be listed. Although there are research hypotheses, no hypotheses will be prospectively tested in this study.

Pharmacokinetics: Nivolumab and varlilumab end of infusion and trough (Cmin) concentration will be tabulated by summary statistics. This data may also be pooled with other datasets for population PK analysis which will be part of a separate report.

Immunogenicity Analyses: A listing will be provided of all available immunogenicity data. Additionally, a listing of immunogenicity data from those patients with at least one positive anti-drug antibody (ADA) at any time point will be provided. The frequency of patients with at least one positive ADA assessment, and frequency of patients who develop ADA after a negative baseline assessment will be provided. To examine the potential relationship between immunogenicity and safety, the frequency and type of AEs of special interest may be examined by overall immunogenicity status. The relationship between immunogenicity and clinical outcome may also be examined.

Efficacy Analyses: The primary analyses of tumor response and progression will be by RECIST 1.1. Analyses will be presented by study phase, disease type and dose level, depending on data availability. The crude objective response rate (ORR) and corresponding confidence interval will be tabulated for the response-evaluable population. Individual best overall response (BOR) will be listed and similarly tabulated. Overall and landmark (e.g., at 24 weeks) progression-free survival (PFS) and duration of response (DOR) will be estimated by Kaplan-Meier methodology, and the corresponding confidence interval will be provided. Individual changes in the tumor burden over time will be presented graphically for each tumor type. Overall survival will be assessed by Kaplan-Meier plots; medians and landmark analysis at two and three years will be calculated for each tumor type. Supplementary analyses of tumor response and progression may also be performed using "irRECIST" criteria (in which new lesions do not constitute progression, but contribute to the calculated sum of diameter of all measurable disease) and/or performed by a central IRC blinded to investigator assessments.

Overall Objective Response Rate (ORR): ORR is defined as the proportion of patients who achieve best overall response of complete or partial response at any time after initiation of study treatment (prior to initiation of alternate anticancer treatment). The crude objective response rate and corresponding confidence interval will be tabulated for the response-evaluable population. Individual best overall response (BOR) will be listed and similarly tabulated. The estimate of the ORR will be calculated for each Phase II cohort based on the maximum likelihood estimator (i.e., crude proportion of patients whose best overall response is complete response (CR) or partial response (PR)), and will be accompanied by 2-sided 95% exact binomial confidence intervals.

Duration of Objective Response (DOR): DOR is defined as the number of months from the time criteria are first met for either CR or PR, until the first date that progressive disease (PD) is objectively documented. Patients without documented disease progression will be handled as described below for the PFS analysis. The duration of objective response will be summarized descriptively using the Kaplan-Meier method.

Time to Response (TTR): TTR is defined as the number of months from the first dose of study treatment to the time that criteria are first met for either CR or PR. Time to response will be summarized descriptively using the Kaplan-Meier method.

Progression free Survival (PFS): PFS is defined as the number of months from the first dose of study treatment to the earlier of disease progression or death due to any cause. Patients who initiate alternate anticancer therapy in the absence of documented progression will be censored at the latest disease assessment prior to initiation of such therapy. Patients who were last known to be alive and progression-free will be censored at the latest disease assessment. Patients with no baseline or post-baseline disease assessments will be censored at the Day 1 date unless death occurred prior to the first planned assessment (in which case the death will be considered a PFS event). In secondary analyses of PFS, all recorded PFS events will be included in the primary analysis, regardless of initiation of alternate therapy. PFS will be summarized descriptively using the Kaplan-Meier method.

Landmark PFS6: Landmark PFS6 will be calculated according to the methodology described above for PFS.

Overall Survival (OS): OS is defined as the number of months from the first dose of study treatment to the date of death due to any cause. Patients who are alive or lost to follow-up as of a data analysis cutoff date will be right-censored. The censoring date will be determined from the patients' date of last contact. OS will be assessed by Kaplan-Meier plots.

Landmark OS: OS24 and OS36 will be calculated according to the methodology described above for OS.

Safety Analysis: Safety and tolerability will be assessed by incidence, severity, and changes from baseline of all relevant parameters including AEs, DLT, ECGs, laboratory values, and vital signs.

Safety data analysis will be conducted on all patients receiving at least one dose of either study drug. AEs will be coded using the latest available version of the Medical Dictionary for Regulatory Activities (MedDRA). Treatment-emergent AEs are defined as AEs that start on or after the first day study drug is administered. The number and percentage of patients experiencing one or more treatment-emergent AEs will be summarized by treatment cohort, relationship to study drug, and severity. A patient reporting multiple cases of the same AE will be counted once within each system organ class and similarly counted once within each preferred term. Unless specified otherwise, the denominator for these calculations will be based on the number of patients in each treatment cohort who receive at least one (1) dose of study drug, irrespective of the total number of doses administered. Additional summaries may also be provided for SAEs and events resulting in the permanent discontinuation of therapy. All AEs will be included in individual patient data listings.

Laboratory parameters will be summarized using descriptive statistics, by post-dosing shifts relative to baseline, and in data listings. Vital sign results (systolic and diastolic blood pressure, pulse, respiration, and temperature) will be summarized by changes from baseline values using descriptive statistics. ECG results will be evaluated by the investigator and abnormalities, if present, will be listed.

Pharmacokinetics: Nivolumab and varlilumab end of infusion and trough (Cmin) concentration will be tabulated by summary statistics. This data may also be pooled with other datasets for population PK analysis which will be part of a separate report.

Immunogenicity Analyses: A listing will be provided of all available immunogenicity data. Additionally, a listing of immunogenicity data from those patients with at least one positive anti-drug antibody (ADA) at any time point will be provided. The frequency of patients with at least one positive ADA assessment, and frequency of patients who develop ADA after a negative baseline assessment will be provided. To examine the potential relationship between immunogenicity and safety, the frequency and type of AEs of special interest may be examined by overall immunogenicity status. The relationship between immunogenicity and clinical outcome may also be examined.

Biomarker Analyses: The pharmacodynamic effect on tumor infiltrating lymphocytes (TILs) and other tumor markers in patients who undergo biopsy will be assessed by summary statistics and plots. In addition, the correlation of TIL changes and tumor marker expression with measures of peripheral blood markers will be explored graphically and by appropriate statistics based on data availability. The pharmacodynamic effect of nivolumab and varlilumab on biomarkers in peripheral blood and serum proteins will be assessed by summary statistics, and investigated graphically to explore patterns of change over time, and how the patterns differ among dose levels or exposure. If there is a meaningful indication in the pattern over time, further analysis (e.g., by linear mixed model) may be performed to characterize the relationship. Associations between biomarker measures from peripheral blood or tumor biopsy and clinical outcomes will also be explored graphically, and further assessed as needed by methods such as, but not limited to, logistic regression, and characterized by appropriate statistics.

Tumor-Specific Inclusion/Exclusion Criteria

Head and Neck

Inclusion Criteria:
1. Histologically confirmed recurrent or metastatic SCCHN (oral cavity, pharynx, larynx), stage III/IV and not amenable to local therapy with curative intent (surgery or radiation therapy with or without chemotherapy)
2. If primary is oropharyngeal: documentation of p16-status to determine human papillomavirus (HPV) status of tumor
3. Tumor progression or recurrence within 6 months of last dose of platinum therapy in the adjuvant (i.e., with radiation after surgery), primary (i.e., with radiation), recurrent, or metastatic setting. Clinical progression after platinum therapy is an allowable event for entry and is defined as progression of a lesion at least 10 mm in size that is amenable to caliper measurement (e.g., superficial skin lesion as per RECIST 1.1) or a lesion that has been visualized and photographically recorded with measurements and shown to have progressed.

Exclusion Criteria:
1. Active brain metastases or leptomeningeal metastases are not allowed. Subjects with brain metastases are eligible if these have been treated and there is no magnetic resonance imaging (except where contraindicated in which CT scan is acceptable) evidence of progression for at least 8 weeks after treatment is complete and within 28 days prior to first dose of study drug administration. Cases, including base of skull lesions without definitive evidence of dural or brain parenchymal involvement, should be discussed with the medical monitor. There must also be no requirement for immunosuppressive doses of systemic corticosteroids (>10 mg/day prednisone equivalents) for at least 2 weeks prior to study drug administration.
2. Histologically confirmed recurrent or metastatic carcinoma of the nasopharynx and salivary gland or non-squamous histologies (e.g., mucosal melanoma) are not allowed.

Ovarian Cancer

Inclusion Criteria:
1. All subjects must have recurrent or persistent epithelial ovarian, fallopian tube or primary peritoneal carcinoma. Histologic documentation of the tumor is required via the pathology report from either original diagnosis or subsequent relapses.
2. All subjects must have received a platinum-taxane based chemotherapy regimen as their frontline therapy for ovarian carcinoma.

Exclusion Criteria:
1. Subjects with a histologic diagnosis of borderline, low malignant potential epithelial carcinoma.

Melanoma

Inclusion Criteria:
1. Subjects must have a histologically confirmed diagnosis of melanoma with advanced disease (previously treated, therapy-refractory or recurrent Stage III (unresectable) or Stage IV)
2. Either of the following:
   a. Patients with disease no longer controlled by surgery, chemotherapy, or radiotherapy; and disease refractory to or relapsed after standard therapy (including high-dose interleukin-2).
   b. Treatment naïve subjects (i.e., no prior systemic anticancer therapy for unresectable or metastatic melanoma). Note that prior adjuvant or neoadjuvant melanoma therapy is permitted if it was completed at least 6 weeks prior to receipt of study treatment, and all related adverse events have either returned to baseline or stabilized.
3. Subjects must have known BRAF V600 mutation status or consent to BRAF V600 mutation testing per local institutional standards during the Screening Period Exclusion Criteria:
1. No nitrosoureas (e.g., carmustine or lomustine) within the past 6 weeks and during study treatment.
2. Ocular melanoma Non-Small Cell Lung Cancer Inclusion Criteria:
1. Subjects with refractory or recurrent histologically or cytologically confirmed non-small cell lung cancer (NSCLC).
2. Malignancy must be deemed unresectable.
3. If EGFR mutated (based on the site determined EGFR mutation test), then subjects may have received EGFR TKI, if completed at least two weeks prior to receipt of study treatment
4. Non-squamous histology, squamous adenosquamous histology, or NSCLC not otherwise specified (NOS) histology after completion of treatment with at least 4 cycles of platinum doublet chemotherapy with or without bevacizumab Recurrent and Metastatic Colon Cancer Inclusion Criteria:
1. Histologically confirmed CRC
2. Metastatic or recurrent CRC
3. Prior treatment:
   a. Progression during, after, or been intolerant following the last administration of approved standard therapies, which must include at minimum a fluoropyrimidine, oxaliplatin, and irinotecan, as well as at least one of the following agents, if approved or in standard national guidelines, bevacizumab, cetuximab or panitumumab (if KRAS wild type), and regorafenib.

OR b. Subject actively refuses chemotherapy for the treatment of metastatic (Stage IV) or locally advanced disease considered as standard treatment for this disease stage, despite being informed by the investigator about the treatment options. The subject's refusal must be thoroughly documented. The investigator will discuss each individual subject refusing chemotherapy with the sponsor's medical monitor to confirm eligibility.

Example 2

Figure 2B:
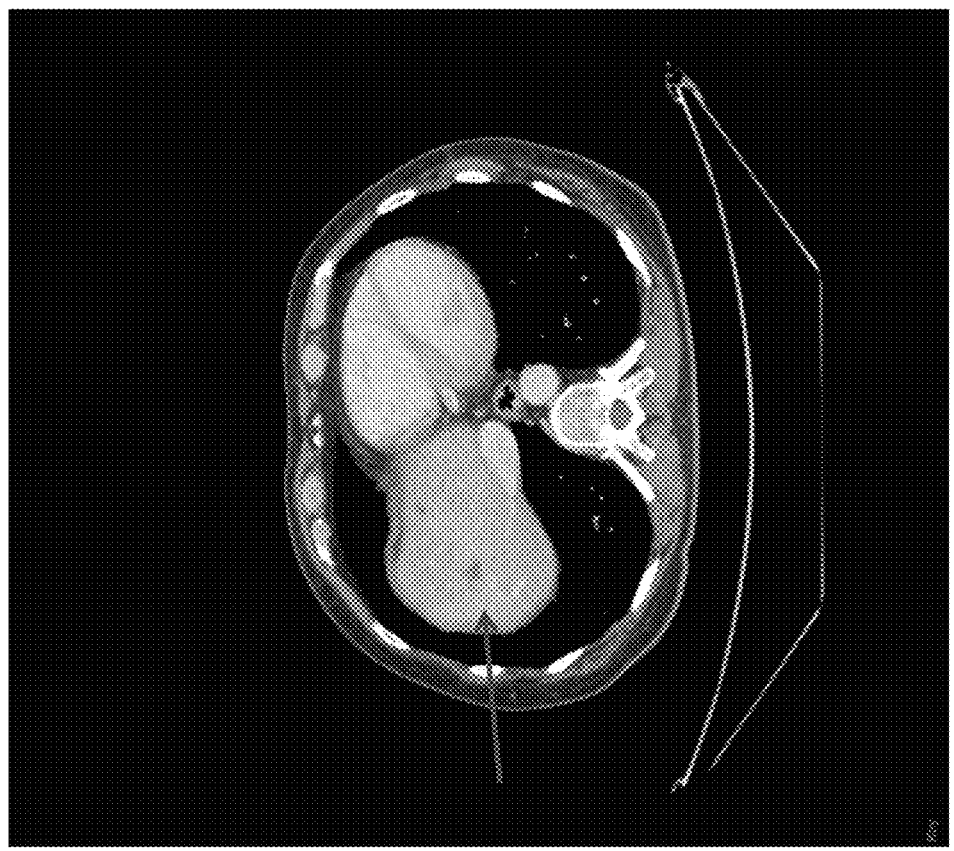
FIG. 2A and FIG. 2B show a computed tomography (CT) comparison of a liver lesion in a microsatellite instability (MSI)-stable colorectal cancer patient treated with varlilumab in combination with nivolumab. The second measurement (FIG. 2B) was about two months after the first measurement (FIG. 2A).
Figure 2A:
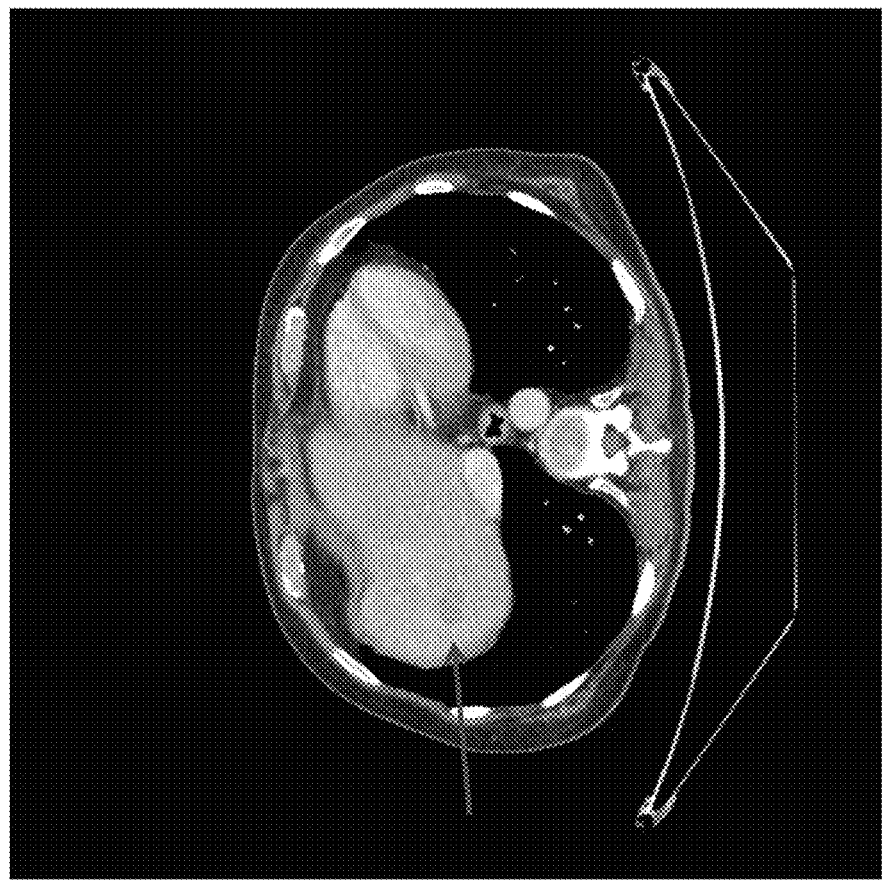
Figure 3A:
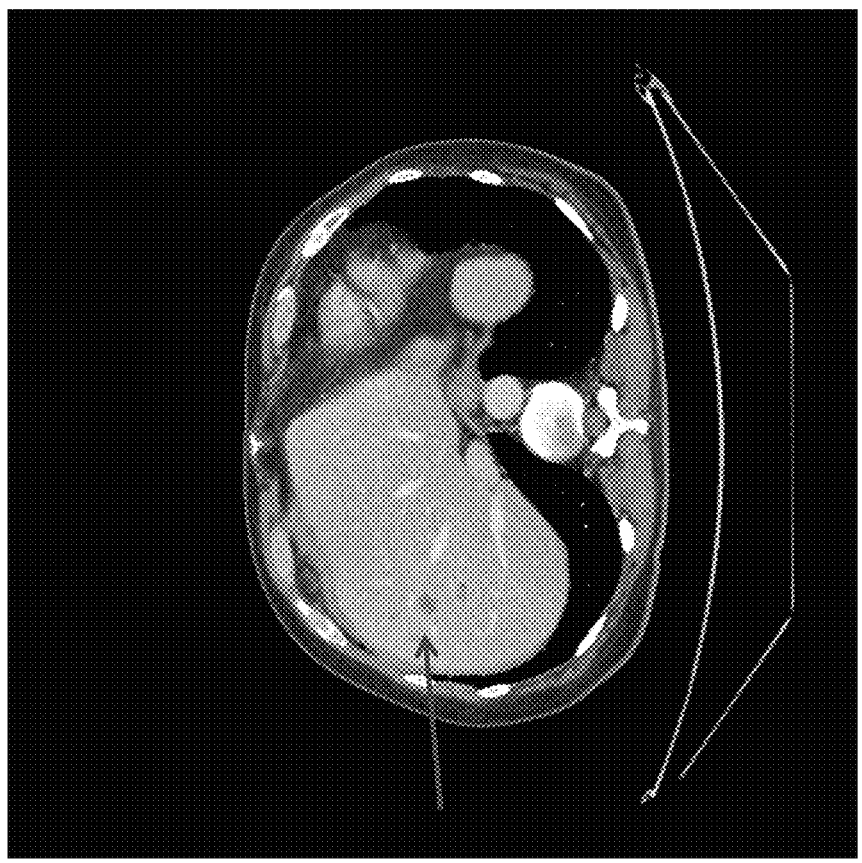
FIG. 3A.
Figure 3B:
FIG. 3B show CT scans of a liver lesion in an MSI-stable colorectal cancer patient treated with varlilumab in combination with nivolumab. The second measurement (FIG. 3B) was about two months after the first measurement (FIG. 3A).
Figure 4A:
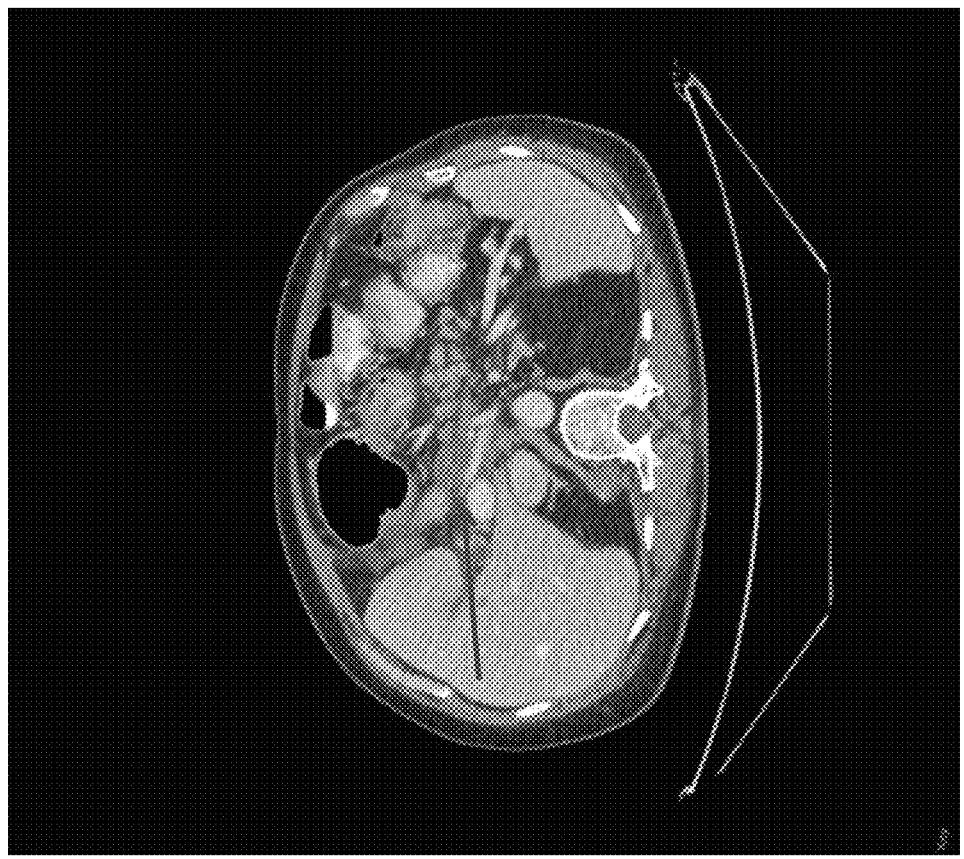
FIG. 4A and FIG. 4B show CT scans of a retroperitoneal lymph node in an MSI-stable colorectal cancer patient treated with varlilumab in combination with nivolumab. The second measurement (FIG. 4B) was about two months after the first measurement (FIG. 4A).
Figure 4B:
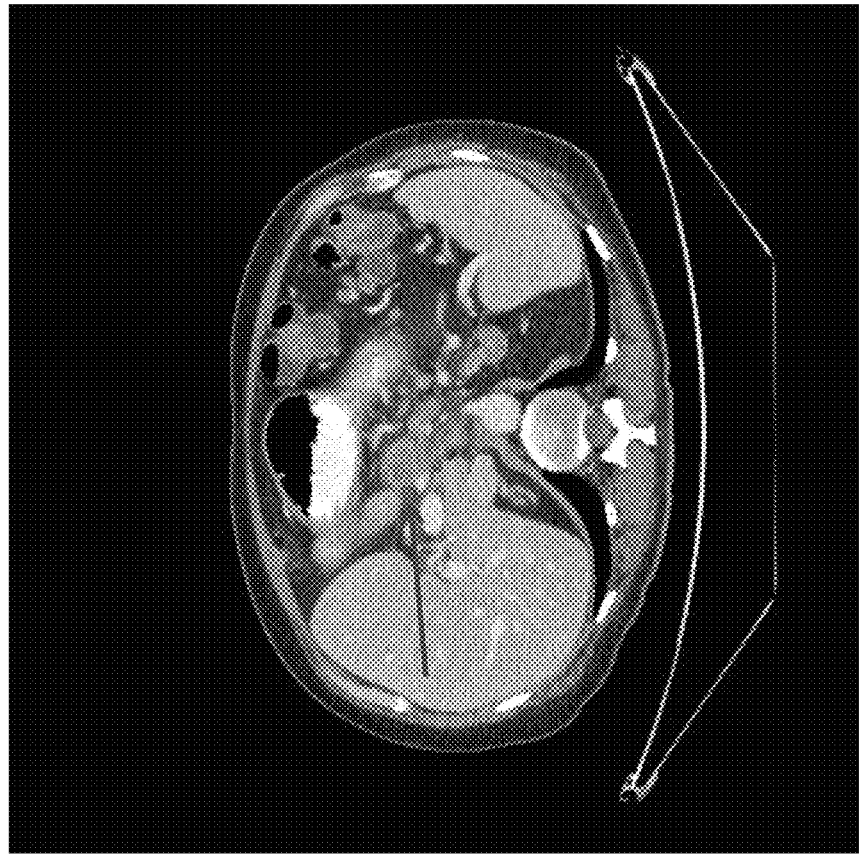
Figure 5A:
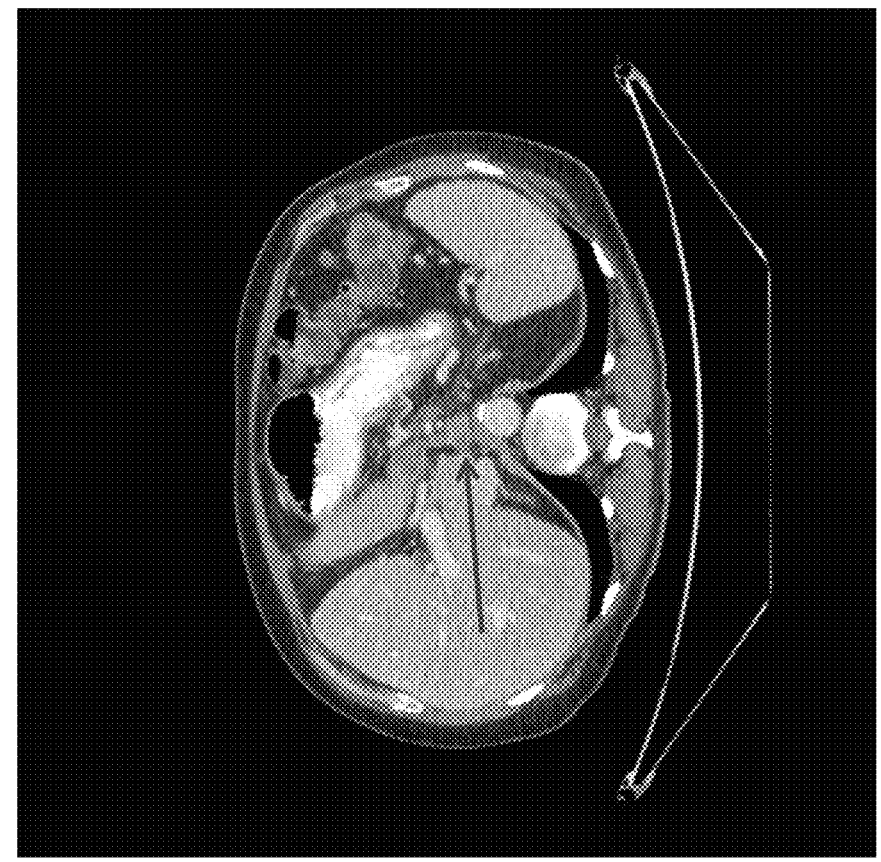
FIG. 5A and FIG. 5B show additional CT scans of a retroperitoneal lymph node in an MSI-stable colorectal cancer patient treated with varlilumab in combination with nivolumab. The second measurement (FIG. 5B) was about two months after the first measurement (FIG. 5A).
Figure 5B:
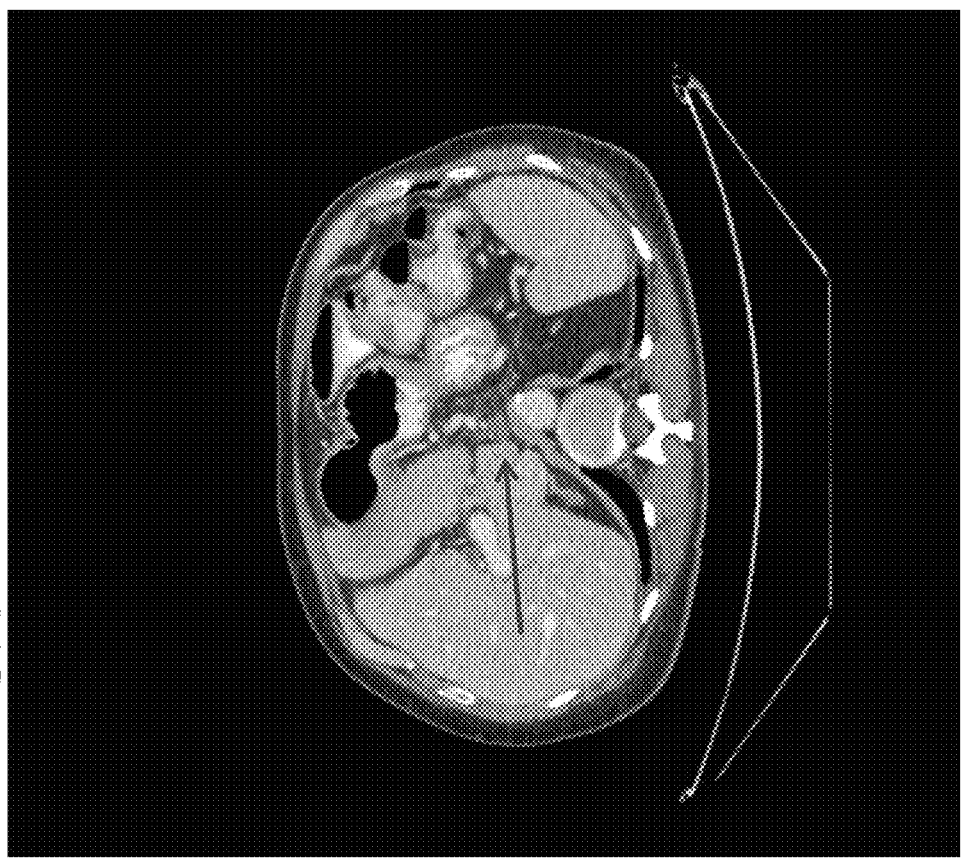
Figure 6B:
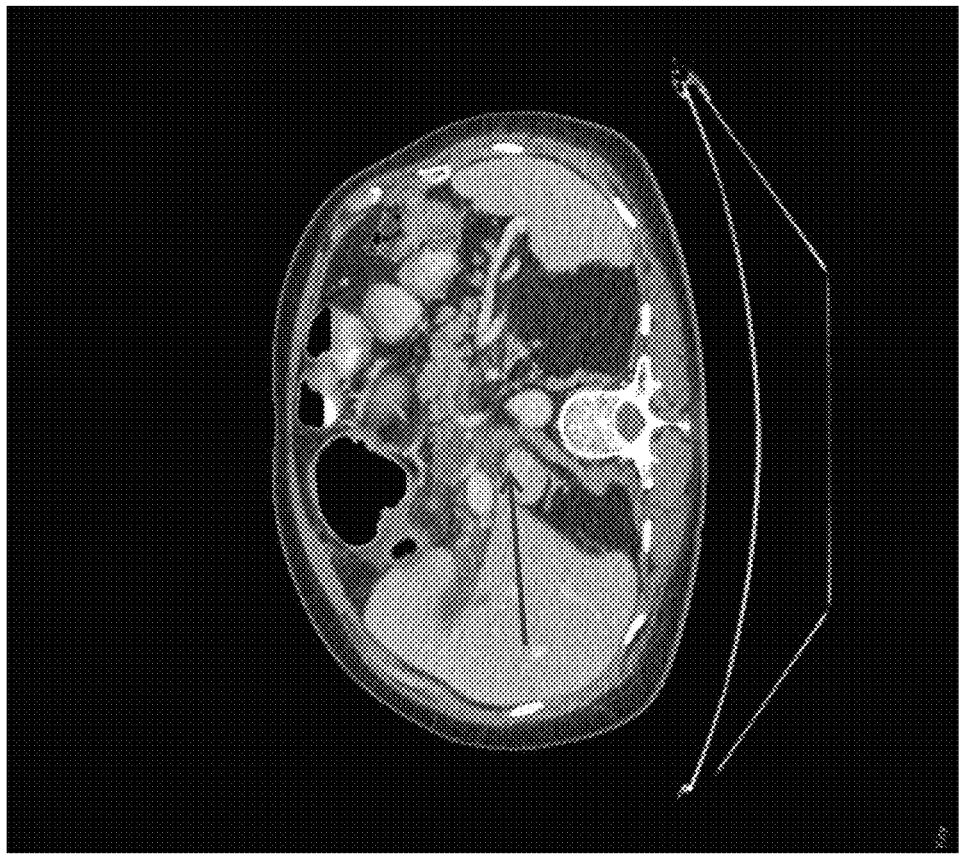
FIG. 6A and FIG. 6B show CT scans of a lymph node in an MSI-stable colorectal cancer patient treated with varlilumab in combination with nivolumab. The second measurement (FIG. 6B) was about two months after the first measurement (FIG. 6A).
Figure 6A:
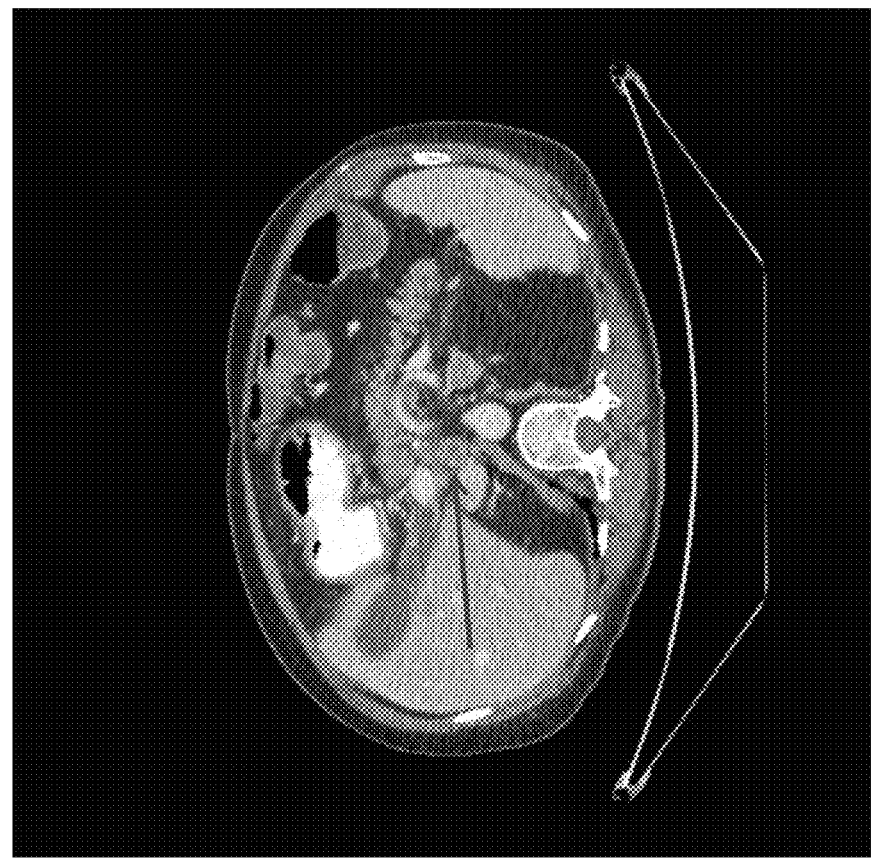
Figure 7B:
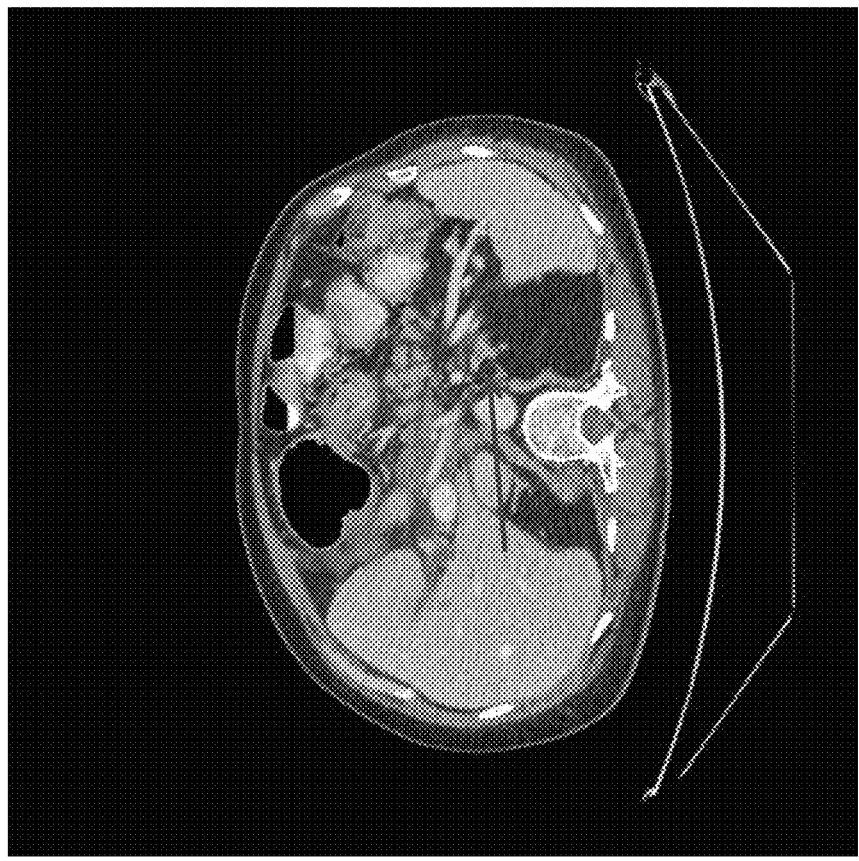
FIG. 7A and FIG. 7B show CT scans of a left adrenal metastasis in an MSI-stable colorectal cancer patient treated with varlilumab in combination with nivolumab. The second measurement (FIG. 7B) was about two months after the first measurement (FIG. 7A).
Figure 7A:
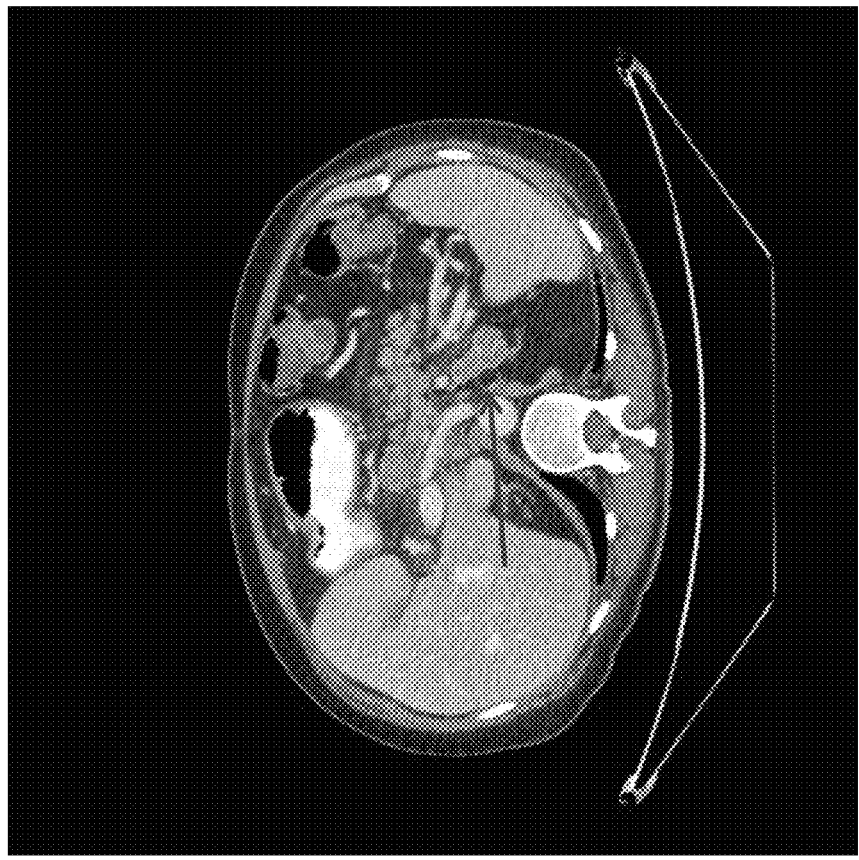

Clinical Case Example of an MSI-Stable Patient Treated with Nivolumab+Varlilumab A colorectal cancer patient that was microsatellite instability stable was treated with 1 mg/kg varlilumab in combination with 3 mg/kg of nivolumab. After four infusions of the treatment, the patient met the criteria for a partial response. A computed tomography (CT) comparison of a liver lesion in this patient dated Apr. 23, 2015 and Jun. 29, 2015 is provided in FIGS. 2A-2B. CT scans of a liver lesion in this patient dated Apr. 23, 2015 and Jun. 29, 2015 are provided in FIGS. 3A-3B. CT scans of a retroperitoneal lymph node in this patient dated Apr. 23, 2015 and Jun. 29, 2015 are provided in FIGS. 4A-4B. Additional CT scans of a retroperitoneal lymph node in this patient dated Apr. 23, 2015 and Jun. 29, 2015 are provided in FIGS. 5A-5B. CT scans of a lymph node in this patient dated Apr. 23, 2015 and Jun. 29, 2015 are provided in FIGS. 6A-6B. CT scans of a left adrenal metastasis in this patient dated Apr. 23, 2015 and Jun. 29, 2015 are provided in FIGS. 7A-7B. Based on the scans, in general the disease process appears to be improved. Numerous small hepatic lesions which are smaller when compared to the previous study. The retroperitoneal and mesenteric adenopathy is significantly smaller when compared to the previous study. The left adrenal lesions have essentially resolved. There is a stable right renal cyst.

TABLE 3

Table 3. Schedule of Assessments

| Visit Window[1] | Screen[2] -28 to -1 | Cycle 1 | | | | | Subsequent Cycles | | | | End of Treatment[4] |
|---|---|---|---|---|---|---|---|---|---|---|---|
| | | Dose 1 | Day 2 | Dose 2 | Dose 3 ±2 days | Dose 4 | Dose 1 | Dose 2 | Dose 3 ±2 days | Dose 4 | |
| Informed consent[2] | X | | | | | | | | | | |
| Demographics and medical history[6] | X | X | | | | | | | | | |
| Pregnancy test[1,7] | X | X | | | X | | X | | X | | |
| HPV (SCCHN patients only)[1] | X | | | | | | | | | | |
| Hepatitis B/C[1,8] | X | | | | | | | | | | |
| Hematology[10] | X | X[9,10] | X | X[10] | X[10] | X[10] | X[10] | X[10] | X[10] | X[10] | X |
| Serum chemistry/liver function tests'[10] | X | X[9,10] | | X[10] | X[10] | X[10] | X[10] | X[10] | X[10] | X[10] | X |
| Thyroid function[10] | X | X[9,10] | | X[10] | X[10] | X[10] | X[10] | X[10] | X[10] | X[10] | X[10] |
| Urinalysis'[10] | X | X[9] | | | | | X | | | | X |
| ECOG performance status | X | X | | X | X | X | X | X | X | X | X |
| Vital signs[11] | X | X | | X | X | X | X | X | X | X | X |
| Physical examination[12] | X | X | | X | X | X | X | X | X | X | X |
| ECG | X | | | | | | | | | | X |
| Chest radiography | X | | | | | | | | | | |
| Blood for RNA (PaxGene tube)[13] | | X | X | | | | X[14] | | | | |
| Blood for flow cytometry and cellular immune studies[13,15,16] | | X | | X | | | X[14] | | | | |
| Immunogenicity[13,17] | | X | | | | | | | | | X |
| PK/serum cytokines[13,18] | | X | X | X | X | X | | | | | |
| Submission of archival tumor tissue[19] | X | | | | | | | | | | |
| Tumor biopsy/Peripheral blood[13,20,21] | X | | | | X | | | | | | X |
| Diagnostic Imaging/Response Assessment[22] | X | | | | | | | | | | |
| Varlilumab administration[23] | | X | | X | X | X | X | X | X | X | |
| Nivolumab administration[23] | | X | | X | X | X | X | X | X | X | |
| Concomitant medications[24] | X | X | X | X | X | X | X | X | X | X | X |
| Adverse events[24] | | X | X | X | X | X | X | X | X | X | X |
| Survival status/response to subsequent therapie[25] | | | | | | | | | | | |

| Visit Window[1] | Clinical Follow-up | | | Disease Assessment | Survival |
|---|---|---|---|---|---|
| | Day 30 post-tx | Day 60 post-tx ±7 days | Day 100 post-tx | Every 8 weeks (±7 days) | Follow-up[5] Every 12 (±2) weeks |
| Informed consent[2] | | | | | |
| Demographics and medical history[6] | | | | | |
| Pregnancy test[1,7] | | | | | |
| HPV (SCCHN patients only)[1] | | | | | |
| Hepatitis B/C[1,8] | | | | | |
| Hematology[10] | X | X | X | | |
| Serum chemistry/liver function tests'[10] | X | X | X | | |
| Thyroid function[10] | | | | | |
| Urinalysis'[10] | | | | | |
| ECOG performance status | X | X | X | | |
| Vital signs[11] | X | X | X | | |
| Physical examination[12] | X | X | X | | |
| ECG | | | | | |
| Chest radiography | | | | | |
| Blood for RNA (PaxGene tube)[13] | | | | | |

TABLE 3-continued

Table 3. Schedule of Assessments

| Assessment | | | | | |
|---|---|---|---|---|---|
| Blood for flow cytometry and cellular immune studies[13, 15, 16] | | | | | |
| Immunogenicity[13, 17] | | | X | | |
| PK/serum cytokines[13, 18] | | | | | |
| Submission of archival tumor tissue[19] | | | | | |
| Tumor biopsy/Peripheral blood[13, 20, 21] | | | | | |
| Diagnostic Imaging/Response Assessment[22] | | | | X[22] | |
| Varlilumab administration[23] | | | | | |
| Nivolumab administration[23] | | | | | |
| Concomitant medications[24] | X | X | X | X | X |
| Adverse events[24] | X | X | X | X | X |
| Survival status/response to subsequent therapie[25] | | | | X[5] | X |

Table Footnotes:

[1] A delay in study treatment or performance of study visits due to holidays, weekends, inclement weather or other unforeseen circumstances will be permitted and not considered a protocol violation. However, significant delays (i.e., greater than one week) due to these reasons should be discussed with the Celldex Medical Monitor to reach consensus on subsequent scheduling.

[2] Informed consent may be signed at any time prior to or during the screening window. No study-specific procedures will be performed prior to receipt of signed Informed Consent (and, if applicable, HIPAA authorization). However, assessments performed according to standard of care prior to receipt of Informed Consent may be utilized to fulfill the screening requirement, if completed within the required window for screening.

[3] In the absence of confirmed progression or clinical deterioration suggesting that no further benefit from treatment is likely, nivolumab may continue for up to a total of 12 treatment cycles, and varlilumab may continue for up to a total of 3 treatment cycles. After completion of the $3^{rd}$ treatment cycle, upon consultation with and agreement by the Celldex Medical Monitor, patients who show evidence of an emerging response may receive one additional cycle of varlilumab for a total of 4 treatment cycles. Retreatment may begin immediately after (or on the same date as) the disease assessment, according to the assessments starting with Day 1. Patients will enter the Clinical Follow-up Period after discontinuation of both study treatments.

[4] The End of Treatment visit should be performed within 28 days after last study drug dosing and prior to initiation of alternate therapies. This visit may be combined with the 30-day post-treatment follow-up visit, if the windows overlap, with required assessments completed once for the combined visit.

[5] Subsequent to the Clinical Follow-up, all patients will be followed at 12 (±2) week intervals for up to 3 years following the first dose of study treatment. However, for any patients who continue to undergo Disease Assessment Visits, the survival contacts may occur during those visits.

[6] Medical history includes demography, prior/current conditions, prior cancer history and treatments, and surgical history. At Day 1, medical history is updated prior to administration of study drug.

[7] Pregnancy tests are required only for women of childbearing potential (excluding patients who are post-menopausal with absence of menses for at least 1 year and/or surgically sterilized). A serum pregnancy test is required at screening, while urine or serum pregnancy tests are required within 24 hours prior to dosing for dose 1 and dose 3 of each treatment cycle. The Cycle 1 Day 1 pregnancy test does not need to be repeated if the screening pregnancy test was done within the 24 hours prior to dosing.

[8] Tests for hepatitis B surface antigen and hepatitis C (antibody screen and if positive confirmed by RNA analysis). If positive results are not indicative of a true active or chronic infection, the patient can be enrolled after discussion with, and agreement by, the Celldex Medical Monitor.

[9] Assessments do not need to be repeated if performed within 72 hours of Day 1 dosing as part of the screening assessment.

[10] Laboratory assessments will include the following. On study treatment days, hematology and chemistry tests (at a minimum, the tests indicated with an asterisk below) must be performed within 72 hours prior to dosing, and results must be reviewed prior to study treatment administration. For all other laboratory tests, results from the prior visit must be reviewed before the administration of study treatment. All toxicity (including laboratory abnormalities, but excluding the specific exceptions noted previously) associated with study treatment must resolve to grade 1 or less prior to administration of the next dose.

| Hematology: | Clinical Chemistry: | Urinalysis |
|---|---|---|
| Hemoglobin* | Sodium* | Protein |
| Hematocrit* | Potassium* | Glucose |
| Mean corpuscular volume (MCV) | Chloride | Specific gravity |
| Erythrocyte count (RBC) | Bicarbonate | Blood |
| Leukocytes (WBC)* | Glucose (nonfasting) | Microscopic examination will be |
| Platelets* | Blood urea nitrogen (BUN)* | performed if indicated |
| Differential:* | Creatinine* | Thyroid Function* |
| Neutrophils | Calcium | TSH |
| Lymphocytes | Magnesium | Free T4 |
| Monocytes | Phosphate | Free T3 |
| Eosinophils | Alkaline phosphatase* | Thyroid function tests are not |
| Basophils | Alanine transaminase (ALT/SGPT)* | required at Dose 2 and Dose 4 |
| Aspartate transaminase (AST/SGOT)* | | starting at cycle 3 and all |
| Differential should be reported | Total protein | subsequent cycles. |
| consistently throughout the | Albumin | Free T4 and free T3 performed at |
| study as either an absolute | Lactate Dehydrogenase (LDH) | screening, and then only if TSH is |
| count (preferred) or as | Total Bilirubin* | abnormal at subsequent |
| a percentage. | Uric acid | visits. |
| | Amylase* | |
| | Lipase* | |

If thyroid function tests are abnormal at end of treatment, continue monitoring to resolution or clinical stabilization.
* On study treatment days, tests must be performed within 72 hours prior to dosing, and results must be reviewed prior to study treatment administration

[11] Vital signs should include heart rate, respiratory rate, blood pressure, temperature and weight. Height should be recorded during screening only. On study treatment days, vital signs should be assessed prior to initiation of the varlilumab infusion; at 45 (±10) minutes during the varlilumab infusion; within 10 minutes after completion of the varlilumab infusion; within 10 minutes prior to initiation of the nivolumab infusion; at 30 (±10) minutes during the nivolumab infusion, and within 10 minutes after completion of the nivolumab infusion. Weight is recorded only once at each visit.

TABLE 3-continued

Table 3. Schedule of Assessments

[12] Complete physical exam should be performed at Screening; thereafter, symptom-directed physical exams are acceptable.
[13] Analyses performed at a central laboratory; sample collection, processing and shipping instructions will be provided separately.
[14] Samples required only for Cycle 2, Dose 1 visit.
[15] Flow cytometry analyses will include but may not be limited to assessment of peripheral blood lymphocyte populations and activation status.
[16] Peripheral blood mononuclear cells will be cryopreserved and may be used for functional studies, which may include, but may not be limited to, analysis of recall responses to CMV, Flu and EBV, mixed lymphocyte response (MLR) or response to tumor antigens. This is a 60-90 mL blood sample. A reduced volume (50 ml) may be drawn if the patient has experienced progressive anemia (hemoglobin decline to less than 60% of lower limit of normal) or has required new blood transfusion for anemia.
[17] Serum samples will be analyzed for antibodies to varlilumab and nivolumab.
[18] On study treatment administration days, samples should be drawn from the arm contralateral to the infusion site prior to the varlilumab infusion, post varlilumab infusion (within 15 minutes), and 3 hours (±15 minutes) following the completion of the varlilumab infusion (approximately 0.5 to 1 hour after completion of the nivolumab infusion). An additional sample should be drawn as soon as possible for any patients who experience an infusion reaction.
[19] Tumor tissue (archived or recent) should be submitted for retrospective biomarker analyses (unless permission of the Celldex Medical Monitor was obtained for enrollment of a patient without available tissue).
[20] As dictated by study eligibility requirements, patients must prospectively consent to undergo pre-treatment and on-treatment biopsies, until Celldex notifies study centers that the requisite number of patients undergoing such biopsies has been reached, or that further data is not needed, for each study phase/cohort. Pre-treatment tissue obtained by biopsy or resection performed according to standard of care may be utilized, provided tissue was obtained within 8 weeks of study entry, and subsequent to the last systemic anticancer therapy received. Post-treatment biopsies (following completion of all study therapy) will be optional for these patients. In addition, all enrolled patients will be given the option of undergoing pre-treatment, on-treatment and post-treatment biopsies if they can be performed with acceptable clinical risk, and with appropriate patient consent. Patients who initially refuse pre-treatment biopsies, but who have clinically meaningful events such as response, disease progression or adverse events of interest, should be offered the opportunity to consent to provide on-treatment and/or post-treatment biopsies. Biopsy sites must be soft tissue tumor lesions that can be biopsied with acceptable clinical risk (as judged by the investigator); are large enough to allow for the collection of tumor tissue using a ≥18 gauge needle with an expected core sample length of 5 mm; and have not been irradiated prior to entry. Biopsy sites must be distinct from RECIST 1.1 target lesions, unless the biopsy is obtained more than 10 days prior to the Screening Disease Assessment. A minimum of 2 passages of the needle core should be obtained. If adequate tissue is not obtained following initial passages of the needle; a repeat passages of the needle may be required performed if possible. Patients unable to undergo repeat passages (at acceptable risk as judged by the investigator) will still be allowed to receive study therapy provided all other eligibility criteria are met. Smaller lesions may be biopsied or smaller gauge needles may be used provided adequate tissue can be collected (similar quantity to amount collected using 18 gauge thickness and 5 mm core length). Biomarkers from tumor biopsies may include measures of TILs and PD-L1 and HLA Class I expression.
[21] All patients who undergo biopsies, either required or optional, will also have peripheral blood collected at the same visit, in order to have matched normal sample. Biomarkers from peripheral blood will include measures of CD27 expression, NK and T cell functional assays, soluble factors, ctDNA, KIR expression on NK cells.
[22] Imaging-based evaluation per RECIST 1.1 should be performed, and tumor markers assessed as standard of care will also be reported. At the sponsor's discretion, scans and measurements may be collected for retrospective review by the IRC. Contrast-enhanced CT of the chest, abdomen, and pelvis, as well all other suspected disease sites is required. MRI exams of the brain, abdomen, and pelvis can be performed in lieu of a CT; however MRI exams of the chest are not recommended. In the event that a chest MRI is performed, a non- contrast chest CT is strongly recommended to evaluate the lung parenchyma. Brain imaging will also be performed on all patients at Screening and repeated at each staging visit for patients with positive screening scans, or if clinically indicated. Lesions identified on bone scans should be confirmed by a CT or MRI at baseline, and, if identified as target lesions due to soft tissue component, they should continue to be followed by the same methodology (i.e., CT or MRI scan). However, bone lesions followed as non-target disease may be subsequently followed by bone scans only. Lesions that cannot be imaged but are assessable by clinical exam may be assessed by color photography including a ruler (preferred method) or measured with calipers. Normally, all target and non-target disease sites should be evaluated at each assessment. However, for patients with non- target bone disease, bone scans need only be repeated every sixteen weeks, or more frequently if clinically indicated. The same imaging modality used at screening should be used throughout the study. Target lesions selected for solid tumor measurements should be those where surgical resection or radiation are not indicated or anticipated. If surgical intervention or localized radiation become indicated (either for palliation or down-staging of previously non-resectable tumor), these interventions should be avoided if clinically feasible until after the second response assessment. A final tumor response assessment should be conducted prior to any intervention or initiation of alternate therapies, in order to document progression and/or confirm an objective response. Patients who undergo surgical resection or radiation in the absence of progression may continue to receive study treatment until remaining lesions meet criteria for progression of disease. For patients who discontinue treatment in the absence of progression, tumor response assessments should continue through clinical and survival follow- up until documented progression or initiation of alternate anticancer therapy.
[23] See previous instructions regarding study treatment administration. Unless indicated otherwise (e.g., PK sampling, vitals), all tests and blood sampling should be performed prior to administration of study drugs, and may be performed up to 72 hours prior to treatment administration if assessments remain within the specified visit window. All toxicity (including laboratory abnormalities, but excluding the specific exceptions noted previously) associated with study treatment must resolve to grade 1 or less prior to administration of the next dose. All patients should be monitored for at least one hour following administration of study treatments; patients who experience any treatment-related adverse events during the observation period should be further monitored as clinically appropriate.
[24] The AE/SAE reporting period begins with the first dose of study treatment while the concomitant medication reporting period begins 28 days prior to the first dose of study treatment. All AEs/SAEs and concomitant medications should be recorded on the CRF through 100 calendar days after the last administration of study treatment. Thereafter, only serious adverse events considered related to study treatment should be reported.
[25] All anticancer surgeries or treatments, and response to those treatments, should be recorded throughout the duration of study follow-up.

What is claimed is:

1. A method for treating a subject afflicted with a tumor comprising administering to the subject in need thereof
    an antibody or an antigen-binding portion thereof that binds specifically to a Programmed Death-1 (PD-1) receptor and inhibits PD-1 activity ("anti-PD-1 antibody") at a dose of about 200 mg or about 240 mg in combination with varlilumab at a dose of 3 mg/kg;
    wherein the anti-PD-1 antibody is selected from the group consisting of nivolumab, pembrolizumab, MEDI0680, and BGB-A317.

2. The method of claim 1, wherein the tumor is colorectal cancer, rectal cancer, colon cancer, lung cancer, melanoma, ovarian cancer, head and neck cancer, or any combination thereof.

3. The method of claim 2, wherein the lung cancer is non-small cell lung cancer (NSCLC).

4. The method of claim 1, wherein the anti-PD-1 antibody is nivolumab.

5. The method of claim 1, wherein
    the anti-PD-1 antibody is pembrolizumab.

6. The method of claim 1, wherein varlilumab is administered once about every 1, 2 or 3 weeks.

7. The method of claim 6, wherein varlilumab is administered once about every 2 weeks.

8. The method of claim 1, wherein the anti-PD-1 antibody and varlilumab are formulated for intravenous administration.

9. The method of claim 1, wherein the anti-PD-1 antibody and varlilumab are administered sequentially.

10. The method of claim 1, wherein the tumor is colon cancer.

11. The method of claim 1, wherein the tumor is PD-L1 positive.

12. The method of claim 1, further comprising measuring PD-L1 expression in the tumor.

13. The method of claim 1, further comprising administering an anti-cancer agent.

14. The method of claim 1, wherein the anti-PD-1 antibody is administered once about every 2 weeks.

15. The method of claim 4, wherein nivolumab is administered at a dose of about 240 mg once about every 2 weeks.

16. The method of claim 15, wherein varlilumab is administered once about every 2 weeks.

17. The method of claim 5, wherein pembrolizumab is administered at a dose of about 200 mg once about every 3 weeks.

18. The method of claim 17, wherein varlilumab is administered once about every 2 weeks.

* * * * *